US008785418B2

(12) United States Patent
Bricout et al.

(10) Patent No.: US 8,785,418 B2
(45) Date of Patent: Jul. 22, 2014

(54) LYOPHILIZATION CAKES OF PROTEASOME INHIBITORS

(75) Inventors: Denis Bricout, Chennevieres sur Marne (FR); Helene Cambourieux, Vitry sur Seine (FR); Michael L. Cappola, Malvern, PA (US); Nicole Frati, Epinay sur Orge (FR); Piyush R. Patel, Wallingford, PA (US)

(73) Assignee: Cephalon, Inc., Frazer, PA (US)

( * ) Notice: Subject to any disclaimer, the term of this patent is extended or adjusted under 35 U.S.C. 154(b) by 7 days.

(21) Appl. No.: 13/248,398

(22) Filed: Sep. 29, 2011

(65) Prior Publication Data

US 2012/0035133 A1 Feb. 9, 2012

Related U.S. Application Data

(63) Continuation of application No. PCT/US2010/029597, filed on Apr. 1, 2010.

(60) Provisional application No. 61/166,529, filed on Apr. 3, 2009, provisional application No. 61/288,955, filed on Dec. 22, 2009.

(30) Foreign Application Priority Data

Apr. 7, 2009 (EP) ..................................... 09305291

(51) Int. Cl.
*A61K 31/69* (2006.01)
(52) U.S. Cl.
USPC ............................................ 514/64; 424/488
(58) Field of Classification Search
None
See application file for complete search history.

(56) References Cited

U.S. PATENT DOCUMENTS

| 4,177,290 | A | 12/1979 | Lafon |
| 4,565,807 | A | 1/1986 | Uekama et al. |
| 4,727,064 | A | 2/1988 | Pitha |
| 4,927,855 | A | 5/1990 | Lafon |
| 5,019,563 | A | 5/1991 | Hunter et al. |
| 5,024,997 | A | 6/1991 | Motola |
| 5,024,998 | A | 6/1991 | Bodor |
| 5,180,745 | A | 1/1993 | Lafon |
| 5,391,576 | A | 2/1995 | Lafon |
| 5,618,845 | A | 4/1997 | Grebow et al. |
| 5,660,845 | A | 8/1997 | Trinh et al. |
| 5,843,347 | A | 12/1998 | Nguyen et al. |
| 5,866,162 | A | 2/1999 | Grattan |
| 5,874,418 | A | 2/1999 | Stella et al. |
| 6,077,871 | A | 6/2000 | Campeta |
| 6,200,968 | B1 | 3/2001 | Dickason et al. |
| RE37,516 | E | 1/2002 | Grebow et al. |
| 6,346,548 | B1 | 2/2002 | Miller et al. |
| 6,455,588 | B1 | 9/2002 | Scammell et al. |
| 7,442,830 | B1 | 10/2008 | Olhava et al. |
| 7,468,383 | B2 | 12/2008 | Bernardini et al. |
| 2002/0169114 | A1 | 11/2002 | Gupta |
| 2005/0240047 | A1 | 10/2005 | Pickersgill et al. |

FOREIGN PATENT DOCUMENTS

| FR | 2 702 968 | 9/1994 |
| JP | 50-116617 | 9/1975 |
| JP | 62-281855 | 12/1987 |
| JP | 03-005438 | 1/1991 |
| WO | WO94/21371 | 9/1994 |
| WO | WO2005/021558 | 3/2005 |
| WO | WO2006/063154 | 6/2006 |

OTHER PUBLICATIONS

International Searching Authority, International Preliminary Report on Patentability for PCT/US2010/029597 dated Oct. 13, 2011.
Stella et al., "Prodrug strategies to overcome poor water solubility," *Advanced Drug Delivery Reviews*, Aug. 24, 2007, 677-694, vol. 59, No. 7, Elsevier BV, Amsterdam, NL.
Piva R et al., "CEP-18770: A novel, orally active proteasome inhibitor with a tumor-selective pharmacologic profile competitive with bortezomib," *Blood*, Mar. 1, 2008, 2765-2775, vol. 111, No. 5.
Dalle Bella M et al., "Cyclodextrins," *Drugs of the Future, Prous Science, ES*, Jan. 1, 1983, 391-394, vol. 8, No. 5.
Supergen, Mitozytrex™ (mitomycin for injection) package insert, Nov. 14, 2002.
Teagarden Dirk L et al., "Practical aspects of lyophiolization using non-aqueous co-solvent systems," *European Journal of Pharmaceutical Sciences*, 2002, 115-133, vol. 15.
Millennium, Velcade® (bortezomib) for injection package insert, Jun. 2005.
Millennium, Velcade® (bortezomib) for injection full prescribing information, Jun. 2008.
Rambert, F.A. et al., *Neuropschychopharmacology*, 1994,10(3S), 169S.
Uekama, K. et al., *CRC Critical Reviews in Therapeutic Drug Carrier Systems*, 1987, 3(1), 1-40.
Parrish, M.A., *Cyclodextrins*.
Loftsson, T., *Pharmaceutical Technology*, 1999, 12, 40-50.
Duchene, D. et al., *Drug Dev. Ind. Pharm.*, 1986, 12(11-13), 2193-2215.
Szente, L. et al., *Journal of Inclusion Phenomena*, 1984, 2, 631-636.
Pagington, J.S., *Chemistry in Britain*, 1987, 455-458.
Wen-Lu, S. et al., *Chemosphere*, 1999, 38(4), 693-698.
Ammar, H. O. et al., *Pharmazie*, 1995, 50, 805-808.
Masson et al., *Journal of Controlled Release*, 1999, 59, 107-118.
Nakanishi, K. et al., *Chem. Pharm. Bull.*, 1992, 40, 1252-1256.
Challa et al., AAPS PharmSciTech, 2005, 6, E329-E357.
Szejtli, J., Introduction and General Overview of Cyclodextrin Chemistry, *Chem. Rev.*, 1998, vol. 98, pp. 1743-1753.
CyDex Presentation on Captisol® (http://www.eydexine.com/maxdoes/cyclodextrin-derivatives.pdf, accessed Apr. 6, 2006).
Loftsson, T. et al., Pharmaceutical Applications of Cyclodextrins, *J. Pharm. Sci.*, 1996, vol. 85, No. 10, pp. 1017-1025.

(Continued)

*Primary Examiner* — Wu-Cheng Winston Shen
*Assistant Examiner* — Theodore R West
(74) *Attorney, Agent, or Firm* — Baker & Hostetler LLP

(57) ABSTRACT

Lyophilized cakes of proteasome inhibitors are described, as well as methods for their production and use.

17 Claims, No Drawings

(56) References Cited

OTHER PUBLICATIONS

Spirichev, V.B. et al., Study of Bioavailability of Different Forms of Synthetic Beta-Carotene in Volunteers, *Vopr. Pitan.*, 1996, vol. 6, pp. 22-26 (abstract only).

Westerberg, G. et al., Beta-Cyclodextrin Reduces Bioavailability of Orally Administered [3H]benzo[a]pyrene in the Rat, *J. Pharm. Sci.*, 2005.

Hostetler, J et al., Effect of Cyclodextrin on the Pharmacology . . . , *Antimicrob. Agents Chemother.*, 1992, vol. 36, No. 2, pp. 477-480.

Nakanishi, K. et al., Effect of the Interaction of Drug-Beta-Cyclodextrin Complex with Bile Salts . . . , *Chem. Pharm. Bull.*, 1989, vol. 37, No. 1, pp. 211-214.

Pitha, Jr. et al., Hydroxypropyl-b-cyclodextrin: Preparation and Characterization, *Int. J. Pharm.*, 1986, vol. 29, pp. 73-82.

Hedges, A., Industrial Application of Cyclodextrins, 1998, vol. 98, pp. 2035-2044.

LYOPHILIZATION CAKES OF PROTEASOME INHIBITORS

CROSS REFERENCE TO RELATED APPLICATIONS

This application is a continuation of International Application PCT/US2010/029597, filed Apr. 1, 2010, which claims the benefit of U.S. Provisional Application No. 61/166,529, filed Apr. 3, 2009, European Patent Application No. 09305291.8, filed Apr. 7, 2009, and U.S. Provisional Application No. 61/288,955, filed Dec. 22, 2009, the disclosures of which are incorporated herein by reference in their entireties.

TECHNICAL FIELD

Lyophilization cakes of proteasome inhibitors, as well as methods for their preparation and use, are described.

BACKGROUND

There are many pharmaceuticals that are known to be highly effective for the treatment of debilitating diseases such as cancer. Unfortunately, many of these pharmaceuticals are not stable to commercial shipping and storage conditions, which may include temperatures above 23° C. (ambient room temperature) and/or relative humidities greater than ambient. In an effort to preserve the integrity of the pharmaceutical, non-routine shipping and storage conditions are sometimes employed. For example, the pharmaceutical is shipped and stored at refrigerated temperatures, under an inert atmosphere, and/or it is provided with instructions to use or discard within just a few days of receipt. Oftentimes, the pharmaceutical must be discarded because it has not retained sufficient integrity during the shipping and storage process. This is undesirable because these sensitive pharmaceuticals are generally developed and manufactured at great expense.

Lyophilization, or "freeze-drying," is a method used in the manufacture of pharmaceuticals. Many technical challenges, for example, identifying appropriate shelf temperatures, product temperatures, vacuum levels, freezing, primary drying parameters, and secondary drying parameters, must be overcome in the development of a commercially viable lyophilization process. In addition, the pharmaceutical is usually sensitive to the lyophilization process, which typically involves the use of water. Moreover, lyophilization usually involves the addition of pharmaceutical excipients, such as bulking agents and the like. The sensitivity of the particular pharmaceutical to excipients is generally unknown and must be exhaustively evaluated.

Another factor in identifying a suitable lyophilization process is the evaluation of the properties of the lyophilized "cake" that is produced. The cake must be stable to the storage and shipping conditions for a reasonable about of time. Additionally, if the pharmaceutical is for injection, the lyophilized cake should be readily reconstituted with an appropriate intravenous solution such as Sodium Chloride for Injection, Sterile Water for Injection, Mannitol I.V., and the like, to form a particulate-free injectable solution. Indeed, lyophilized cakes that do not readily form a clear solution with little to no particulate matter must be discarded.

As such, lyophilization conditions and methods for producing stable, readily reconstitutable lyophilized proteasome inhibitors are needed.

SUMMARY

The present invention is directed to lyophilized cakes comprising (a) a drug, wherein the drug is a compound of Formula I, Formula II, or a pharmaceutically acceptable salt or ester thereof:

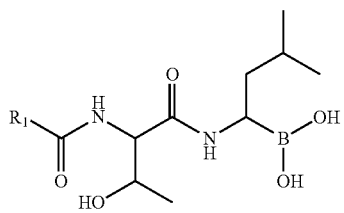

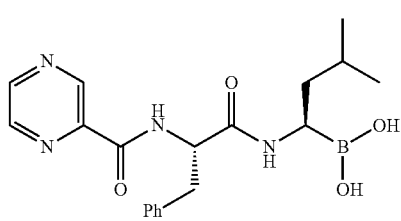

wherein $R_1$ is an optionally substituted 5-, 6-, or 10-membered heteroaryl having at least one N or $R_1$ is an optionally substituted 6- or 10-membered aryl;
(b) a cyclodextrin; and (c) at least one member selected from the group consisting of bulking agents and surfactants. Methods of preparing and using the lyophilized cakes of the invention are also described.

DETAILED DESCRIPTION OF ILLUSTRATIVE EMBODIMENTS

It has now been discovered that the addition of a cyclodextrin to the lyophilized cakes of the described proteasome inhibitors results in cakes that are stable and readily and reproducibly reconstituted to form solutions suitable for injection into humans. Lyophilization processes suitable for use with the described proteasome inhibitors have also been discovered.

Proteasome inhibitors such as those of Formula I:

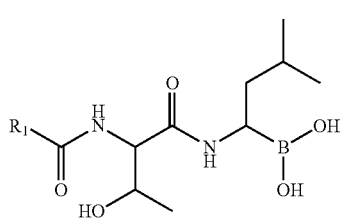

wherein $R_1$ is an optionally substituted 5-, 6-, or 10-membered heteroaryl having at least one N or $R_1$ is an optionally substituted 6- or 10-membered aryl have been described. See U.S. application Ser. No. 11/351, 193, filed Feb. 2, 2006, assigned to Cephalon, Inc., Frazer, Pa., the entirety of which is incorporated herein for all purposes. Such compounds have been demonstrated as useful in the treatment of chronic lymphocytic leukemia, Hodgkin's disease, non-Hodgkin's lymphoma, multiple myeloma or breast cancer. One compound of Formula I in particular, referred to herein as Compound 1:

Compound 1

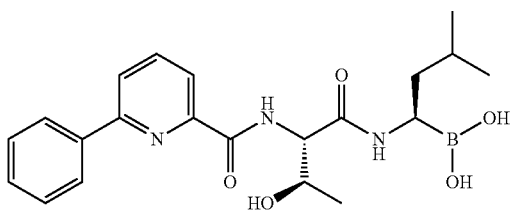

demonstrated strong anti-angiogenic activity and represses RANKL-induced osteoclastoenesis in vitro. Piva, R. R., et al., *Blood*, 1 Mar. 2008, vol 111, No. 5, p 2765-2775. Compound 1 also exhibits a favorable cytotoxicity profile toward normal human epithelial cells, bone marrow progenitors, and bone marrow-derived stromal cells. Id. However, Compound 1 is unstable and subject to degradation upon exposure to air and/or light, with some batches of Compound 1 degrading when stored at temperatures as low as 5° C.

Compound 1 is currently undergoing clinical trials. Since the compound is unstable in solution, it was provided to clinicians in a frozen formulation prior to the present invention, which is inconvenient for distribution and use.

Compounds of Formula I which are envisioned for use in the present invention, include, for example, compounds having the following stereochemistry:

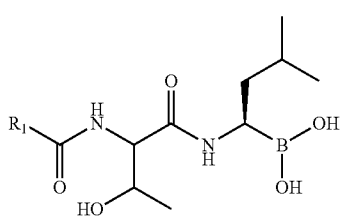

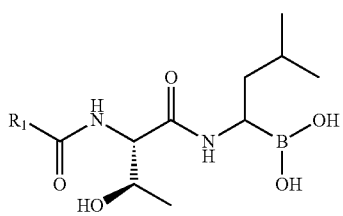

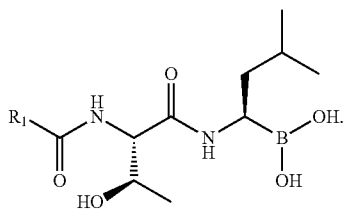

In preferred embodiments, $R^1$ is optionally substituted pyrazinyl, pyridyl, phenyl, thiazolyl, naphthyl, or quinolinyl. Preferably, $R^1$ is substituted. In the most preferred embodiments, $R^1$ is a 5-membered heteroaryl substituted with phenyl, a 6-membered heteroaryl substituted with phenyl, or phenyl substituted with phenyl.

Examples of preferred compounds of Formula I include:

Compound 1

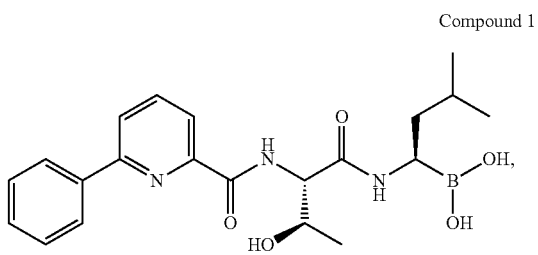 [SMILES: CC(C)C[C@H](NC(=O)[C@@H](NC(=O)c1cccc(-c2ccccc2)n1)[C@@H](C)O)B(O)O]

Compound 2

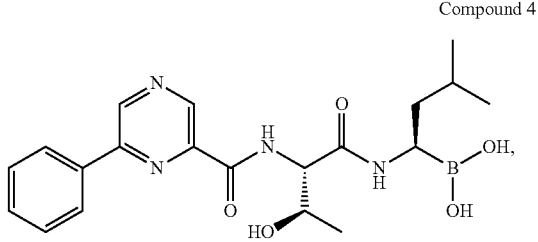

Compound 3

Compound 4

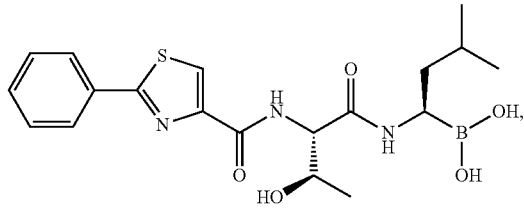

Compound 5

Compound 6

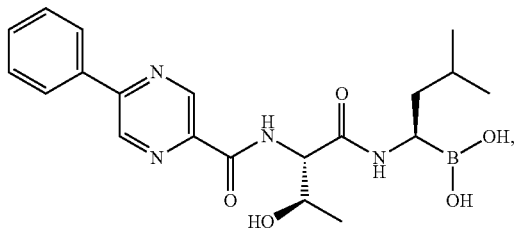

Compound 7

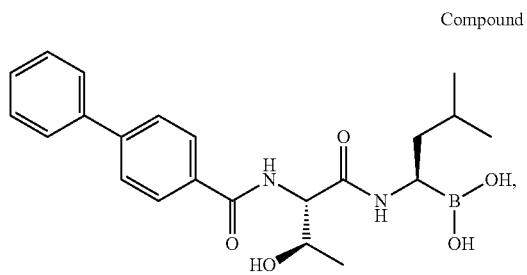

Compound 8

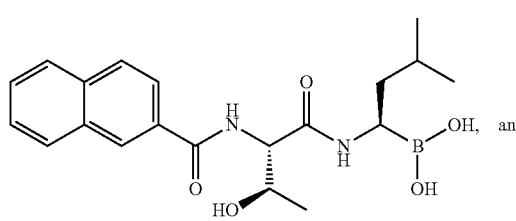
and

Compound 9

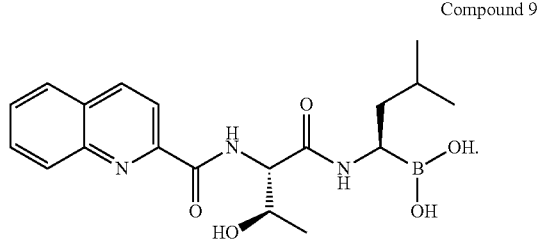

Examples of preferred esters of compounds of Formula I include:

Compound 10

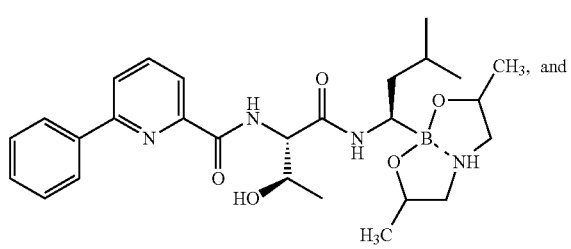
,

Compound 11

The compound of Formula II:

II commonly known as bortezomib, PS-341, or VELCADE®, is a proteasome inhibitor approved in the United States for the treatment of relapsed multiple myeloma and mantle cell lymphoma. See VELCADE® Full Prescribing Information. Presently, bortezomib is provided as a lyophilized powder, containing mannitol as a bulking agent, that the clinician reconstitutes with 0.9% Sodium Chloride. Id. According to the prescribing information, any reconstituted product that is not clear and colorless or that contains particulate matter must be discarded.

Examples of preferred esters of compounds of Formula II include:

Compound 13

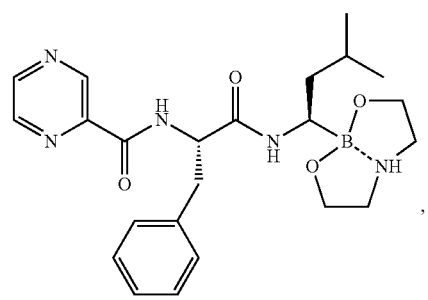
,

Compound 14

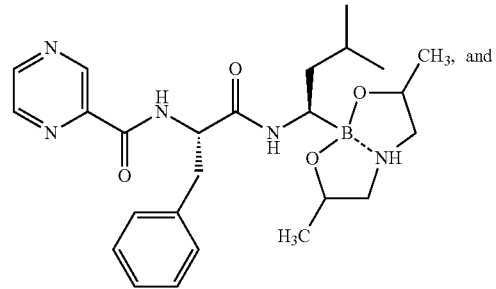

Compound 15

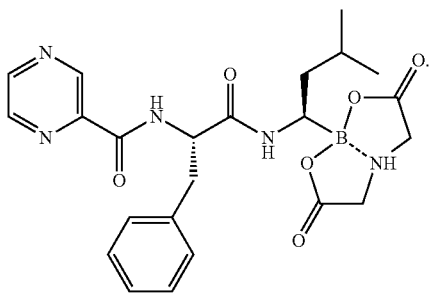

Preferably, the drug is a compound of Formula I or Formula II. Preferably, the drug is a compound of Formula I. In exemplary embodiments, the drug is chosen from Compound 1, Compound 10, Compound 11, Compound 12, Compound 13, Compound 14, Compound 15, and bortezomib. In exemplary embodiments, the drug is chosen from Compound 1, Compound 10, Compound 11, Compound 12, Compound 13, Compound 14, and Compound 15. Preferably, the drug is chosen from Compound 1, Compound 10, Compound 11, Compound 13, Compound 14, and bortezomib. Preferably, the drug is chosen from Compound 1, Compound 10, Compound 11, Compound 13, and Compound 14. Preferably, the drug is chosen from Compound 1, Compound 10, Compound 11, Compound 13, and bortezomib. Preferably, the drug is chosen from Compound 1, Compound 10, Compound 11, and Compound 13. Preferably, the drug is chosen from Compound 1, Compound 10, Compound 13, and bortezomib. Preferably, the drug is chosen from Compound 1, Compound 10, and Compound 13. Preferably, the drug is chosen from Compound 1 and bortezomib. Preferably, the drug is chosen from Compound 1 and Compound 10. In certain embodiments, the drug is Compound 1. In certain embodiments, the drug is bortezomib. In certain embodiments, the drug is Compound 10. In certain embodiments, the drug is Compound 13.

As used herein, "aryl" refers to aromatic carbocyclyl groups including monocyclic or polycyclic aromatic hydrocarbons such as, for example, phenyl, naphthyl, anthracenyl, phenanthrenyl, and the like. In some embodiments, aryl groups have from 6 to about 18 carbon atoms.

As used herein, "heteroaryl" groups are aromatic heterocarbocyclyl groups (i.e., cyclic hydrocarbon groups wherein one or more of the ring-forming carbon atoms of the cyclic hydrocarbon group is replaced by a heteroatom such as O, S, or N) and include monocyclic and polycyclic aromatic hydrocarbons that have at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, and the like. In some embodiments, heteroaryl groups can have from 1 to about 20 carbon atoms, and in further embodiments from about 3 to about 20 carbon atoms. In some embodiments, heteroaryl groups have 1 to about 4, 1 to about 3, or 1 to 2 heteroatoms.

As used herein, "substituted," indicates that at least one hydrogen atom of a chemical group is replaced by a non-hydrogen moiety. Example substituents include F, Cl, Br, I, $C_1$-$C_6$ alkyl, $C_1$-$C_6$ alkenyl, $C_1$-$C_6$, alkynyl, aryl, haloalkyl, $NR^E R^F$, $N_3$, $NO_2$, CN, CNO, CNS, $C(=O)OR^E$, $R^E CO$, $R^E C(=O)O$, $R^E CONR^E$, $R^E R^F NCO$, ureido, $OR^E$, $SR^E$, $SO_2$-alkyl, $SO_2$-aryl, and $SO_2$—$NR^E R^F$, wherein $R^E$ and $R^F$ are each, independently, H or $C_1$-$C_6$ alkyl. When a chemical group herein is "substituted" it may have up to the full valance of substitution, provided the resulting compound is a stable compound or stable structure; for example, a methyl group may be substituted by 1, 2, or 3 substituents, a methylene group may be substituted by 1 or 2 substituents, a phenyl group may be substituted by 1, 2, 3, 4, or 5 substituents, and the like.

The present invention is also applicable to the pharmaceutically acceptable salts of the compounds of Formula I and Formula II. As used herein, "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as boronic acids or carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from a compound of Formula I or II by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The present invention is also applicable to the pharmaceutically acceptable esters of the compounds of Formula I and Formula II. As used herein, "pharmaceutically acceptable ester" refers to derivatives of the disclosed compounds wherein the compound of Formula I or II is modified by making an ester thereof Examples of pharmaceutically acceptable esters include, for example, boronic esters, i.e., an ester derivative of a boronic acid compound, and cyclic boronic esters. Examples of cyclic boronic esters include, but are not limited to, diethanolamine boronic ester, diisopropanolamine boronic ester, aminodiacetic acid boronic ester, pinanediol boronic ester, pinacol boronic ester, 1,2-ethanediol boronic ester, 1,3-propanediol boronic ester, 1,2-propanediol boronic ester, 2,3-butanediol boronic ester, 1,1,2,2-tetramethylethanediol boronic ester, 1,2-diisopropylethanediol boronic ester, 5,6-decanediol boronic ester, 1,2-dicyclohexylethanediol boronic ester, bicyclohexyl-1,1'-diol, and 1,2-diphenyl-1,2-ethanediol boronic ester. Preferably, the boronic ester is a cyclic boronic ester. Preferably, the cyclic boronic ester is a diethanolamine boronic ester, diisopropanolamine boronic ester, or aminodiacetic acid boronic ester; more preferably diethanolamine boronic ester. For example, Compound 10, Compound 11, Compound 12, Compound 13, Compound 14, or Compound 15.

The pharmaceutically acceptable esters of the invention can be prepared from the boronic acid of Formula I or II by conventional chemical methods. Generally, such esters can be prepared by reacting the acid with a stoichiometric amount of an alcohol or diol in water, an organic solvent, or a mixture of the two.

Embodiments of the present invention are directed to lyophilized cakes of a compound of Formula I or Formula II, in combination with a cyclodextrin. "Cyclodextrin" refers to a family of cyclic oligosaccharides typically containing six or more α-D-glucopyranoside units. The cyclodextrins of the present invention can include the natural occurring cyclodextrins and their derivatives. The natural cyclodextrins include α-cyclodextrin, β-cyclodextrin, and γ-cyclodextrin. Derivatives are typically prepared by modifying the hydroxyl groups located on the exterior, or hydrophilic side, of the cyclodextrin. The types and degree of modification, as well as their preparation, are well known in the art. See, for example, Szejtli, J., *Cyclodextrins and Their Inclusion Complexes*, Akadémiai Kiadó: Budapest, 1982; U.S. Pat. No. 5,024,998; U.S. Pat. No. 5,874,418 and U.S. Pat. No. 5,660,845, and references contained therein, all of which are incorporated herein in their entireties.

Any of the natural cyclodextrins can be derivatized. Cyclodextrin derivatives include alkylated cyclodextrins, preferably methyl-, dimethyl-, trimethyl- and ethyl-β-cyclodextrins; hydroxyalkylated cyclodextrins, including hydroxyethyl-, hydroxypropyl-, and dihydroxypropyl-β-cyclodextrin; ethylcarboxymethyl cyclodextrins; sulfate, sulfonate and sulfoalkyl cyclodextrins, preferably β-cyclodextrin sulfate, β-cyclodextrin sulfonate, and β-cyclodextrin sulfobutyl ether; as well as polymeric cyclodextrins. Other cyclodextrin derivatives can be made by substitution of the hydroxy groups with saccharides, such as glucosyl- and maltosyl-β-cyclodextrin.

Preferred cyclodextrins include the naturally occurring cyclodextrins, methyl-β-cyclodextrin, dimethyl-β-cyclodextrin, trimethyl-β-cyclodextrin, 2-hydroxymethyl-β-cyclodextrin, hydroxyethyl-β-cyclodextrin, 2-hydroxypropyl-β-cyclodextrin, 3-hydroxypropyl-β-cyclodextrin, β-cyclodextrin sulfate, β-cyclodextrin sulfonate, or β-cyclodextrin sulfobutyl ether. Most of these are commercially available from such suppliers as Aldrich Chemical Company, Milwaukee Wis. and Wacker Chemicals, New Canaan, Conn. Preferred cyclodextrins include β-cyclodextrin, hydroxypropyl-β-cyclodextrin and β-cyclodextrin sulfobutyl ether. Preferably, the cyclodextrin is hydroxypropyl β cyclodextrin, hydroxypropyl γ cyclodextrin, sulfobutyl ether β-cyclodextrin, or a mixture thereof. Preferred cyclodextrins include hydroxypropyl-β-cyclodextrin and β-cyclodextrin sulfobutyl ether. In the most preferred embodiments, the cyclodextrin is hydroxypropyl β cyclodextrin. One particularly preferred cyclodextrin is KLEPTOSE® HPB, available from Roquette Frères, France.

Preferably, the cyclodextrin is present in an amount effective to stabilize the drug during and/or after, lyophilization. The cyclodextrin will typically be present in an amount up to about 99% w/w of the lyophilized cake. Preferably, the cyclodextrin will be present in an amount from about 20% to about 90% w/w of the lyophilized cake. In preferred embodiments, the cyclodextrin is present in an amount from about 40% to about 70% w/w of the lyophilized cake. Even more preferred are those embodiments wherein the cyclodextrin is present in an amount of from about 45% to about 65% w/w of the lyophilized cake. Most preferred embodiments comprise 40%, 45%, or 55% w/w of cyclodextrin.

The lyophilized cakes of the present invention also include one or more pharmaceutically acceptable excipients. For example, the lyophilized cakes of the invention may contain one or more bulking agents, one or more surfactants, or a combination of one or more bulking agents and one or more surfactants.

Bulking agents that have "generally regarded as safe" (GRAS) status from the United States Food and Drug Administration (FDA) are well known in the art of pharmaceutical lyophilization and tend to strengthen the structure of the resulting lyophilized cake. Bulking agents include saccharides, preferably monosaccharides or oligosaccharides, sugar alcohols, and mixtures thereof. More specifically, bulking agents used in the present invention include sucrose, dextrose, maltose, lactose, sorbitol, glycine, and dextran. A most preferred bulking agent is mannitol.

The bulking agent is typically present in an amount up to about 99% w/w of the lyophilized cake. Preferably, the bulking agent comprises about 20% to about 90% w/w of the lyophilized cake. In preferred embodiments, the bulking agent comprises about 30% to about 60% w/w of the lyophilized cake. In other embodiments, the bulking agent comprises about 35% or about 45% w/w of the lyophilized cake.

Suitable surfactants include any pharmaceutically acceptable surfactant accorded GRAS status by the FDA. Examples include, but are not limited to, polyoxyethylene sorbitan fatty acid esters (polysorbates), sorbitan esters, polyethylene glycol ethers, saturated polyglycolized glycerides, fatty acid esters of polyethylene glycol, hydroxylated lecithins, medium chain monoglycerides, medium chain fatty acid esters, polyethylene/propylene glycol copolymers, polyethylene glycol stearate, and d-α-tocopheryl polyethylene glycol succinate.

Examples of other useful surfactants are saturated polyglycolized glycerides consisting of mono-, di-, or triglycerides; di-fatty acid esters of polyethylene glycol, e.g., Gelucire® 44/14; hydroxylated lecithins, e.g., Centrolene® A; medium chain monoglycerides, e.g., glyceryl monocaprylate (Imwitor® 308, Capmul® MCM C-8); medium chain monoglycerides and diglycerides, e.g., glyceryl caprylate/caprate (Capmul® MCM); polyethylene/propylene glycol copolymers; block copolymers of ethylene oxide and propylene oxide (e.g., Poloxamer 188, Pluronic® F-68); ethoxylated castor oil (e.g., Cremophor® EL); and macrogol 15 hydroxy stearates (e.g., Solutol® HS 15). Some surfactants are solid or semisolid at room temperature, e.g., Poloxamer 188, glyceryl monocaprylate, and Gelucire® 44/14. Additional surfactants are those found in *The Handbook of Pharmaceutical Excipients,* 2nd Ed., published by The Pharmaceutical Press, London and American Pharmaceutical Association (1994), a common text in the field, which is hereby incorporated by reference in its entirety.

Examples of preferred surfactants include polyoxypropylene polyoxyethylene block copolymers, polysorbates, macrogol 15 hydroxy stearates (e.g., Solutol®), polyoxyl 35 castor oils (e.g., Cremophor® EL), polyethoxylated castor oils, and the like, as well as mixtures thereof. Preferably, the surfactant is a polysorbate, i.e., polyoxyethylene sorbitan fatty acid esters, in particular polysorbate 20 (TWEEN 20) or polysorbate 80 (TWEEN 80).

The addition of the surfactant assists in solubilizing of the compound of Formula I or Formula II, or a salt or ester thereof, during the preparation of the pre-lyophilization solution. In many embodiments, a surfactant is not necessary and is not used. Typically, in those embodiments where the surfactant is used, it has been found that at least 2% w/w of the surfactant is beneficial when preparing the pre-lyophilization solution. Ideally, the surfactant should be present in an amount of about 2% to about 10% w/w of the surfactant in the pre-lyophilization solution. Preferably, the pre-lyophilized solutions of the present invention contain about 2% to about 5% w/w, most preferably, about 2% to about 3% w/w of surfactant. After lyophilization, the lyophilized cake will typical comprise about 10% to about 40% w/w of the surfactant. Preferred embodiments will comprise about 15% to about 20% w/w of the surfactant in the lyophilized cake. Other preferred embodiments will comprise about 15% to about 30% w/w of the surfactant in the lyophilized cake.

Other excipients may also be used with the lyophilized cakes of the present invention. Such excipients may include antioxidants, antimicrobials, cryostabilizers, pH modifiers and the like. In certain embodiments, the lyophilized cakes contain a pH modifier. Inclusion of a pH modifier is particularly preferred when an ester of a compound of Formula I or II is used to prepare the lyophilized cake. Representative pH modifiers include acids, bases, and mixtures thereof (e.g., buffers). Examples include mineral acids such as hydrochloric acid and phosphoric acid. Additional examples include acetic acid, sulfuric acid, ascorbic acid, citric acid, lactic acid, tartaric acid, succinic acid, and maleic acid. Buffers include phosphate buffer, acetate buffer, citrate buffer, tartrate buffer, lactate buffer, succinate buffer, maleate buffer, TRIS buffer, glycine buffer, and histidine buffer. A preferred pH modifier is phosphoric acid.

Particularly when an ester of a compound of Formula I or II is used to prepare the lyophilized cake, the pH of the lyophilized cake is preferably adjusted to a pH of about 7 or lower, such as a pH of about 1 to 7. More preferably, the pH of the lyophilized cake is adjusted to a pH of about 6 or lower, such as a pH of about 2 to 6. More preferably, the pH of the lyophilized cake is adjusted to a pH of about 5 or lower, such as a pH of about 3 to 5. More preferably, the pH of the lyophilized cake is adjusted to a pH of about 4 or lower, such as a pH of about 4. The pH of the lyophilized cake may be adjusted by adjusting the pH of the pre-lyophilization solution.

In certain embodiments, the pre-lyophilization solution is prepared with a pharmaceutically acceptable organic solvent. The addition of the alcohol may assist in the solubilizing of the compound of Formula I or Formula II, or a salt or ester thereof, when preparing the pre-lyophilization solution. In certain embodiments, the pre-lyophilization solution will comprise up to about 90% v/v of organic solvent, such as up to about 75% v/v, up to about 60% v/v, or up to about 40% v/v. Preferably, the pre-lyophilization solution comprises about 5% to about 75% v/v of organic solvent, such as about 10% to about 70% v/v. In preferred embodiments, the pre-lyophilization solution comprises about 20% to about 60% v/v of organic solvent, such as about 30% to about 50% v/v. Preferably, the pre-lyophilization solution comprises about 40% v/v of organic solvent.

Suitable organic solvents include solvents that are miscible with water and removable by lyophilization. Examples include alcohols, preferably $C_{1-6}$alcohols such as ethanol, propanol, t-butanol, and propylene glycol, and polar aprotic solvents such as dimethylsulfoxide. A preferred organic solvent is tert-butanol. Typically, about 3% w/w, or less, of the organic solvent will be present in lyophilized cakes of the present invention. Preferably, the organic solvent will be present in an amount of from about 1% w/w, or less, of the lyophilized cake.

Preferred lyophilized cakes of the present invention include those comprising: (a) a compound of Formula I, Formula II, or a pharmaceutically acceptable salt or ester thereof, more preferably a compound of Formula I, Formula II, or a pharmaceutically acceptable ester thereof, more preferably a compound of Formula I or Formula II, more preferably a compound of Formula I, more preferably Compound 1, Compound 10, Compound 11, Compound 12, Compound 13, Compound 14, Compound 15, or bortezomib, more preferably Compound 1, Compound 10, Compound 11, Compound 13, Compound 14, or bortezomib, more preferably Compound 1, Compound 10, Compound 13, or bortezomib, more preferably Compound 1 or bortezomib, more preferably Compound 1 or Compound 10, more preferably Compound 1; (b) a cyclodextrin, preferably hydroxypropyl β cyclodextrin; and (c) a surfactant, preferably polysorbate 20. Particularly preferred lyophilized cakes of the present invention include those comprising: (a) a compound of Formula I, Formula II, or a pharmaceutically acceptable salt or ester thereof, more preferably a compound of Formula I, Formula II, or a pharmaceutically acceptable ester thereof, more preferably a compound of Formula I or Formula II, more preferably a compound of Formula I, more preferably Compound 1, Compound 10, Compound 11, Compound 12, Compound 13, Compound 14, Compound 15, or bortezomib, more preferably Compound 1, Compound 10, Compound 11, Compound 13, Compound 14, or bortezomib, more preferably Compound 1, Compound 10, Compound 13, or bortezomib, more preferably Compound 1 or bortezomib, more preferably Compound 1 or Compound 10, more preferably Compound 1; (b) a cyclodextrin, preferably hydroxypropyl β cyclodextrin; and (c) a bulking agent, preferably mannitol. Other preferred lyophilized cakes of the invention include those comprising: (a) a compound of Formula I, Formula II, or a pharmaceutically acceptable salt or ester thereof, more preferably a compound of Formula I, Formula II, or a pharmaceutically acceptable ester thereof, more preferably a compound of Formula I or Formula II, more preferably a compound of Formula I, more preferably Compound 1, Compound 10, Compound 11, Compound 12, Compound 13, Compound 14, Compound 15, or bortezomib, more preferably Compound 1, Compound 10, Compound 11, Compound 13, Compound 14, or bortezomib, more preferably Compound 1, Compound 10, Compound 13, or bortezomib, more preferably Compound 1 or bortezomib, more preferably Compound 1 or Compound 10, more preferably Compound 1; (b) a cyclodextrin, preferably hydroxypropyl β cyclodextrin; (c) a bulking agent, preferably mannitol; and (d) a surfactant, preferably polysorbate 20. Any of the lyophilized cakes of the invention may further comprise an organic solvent, such as a $C_{1-6}$alcohol, preferably tert-butanol, preferably in an amount less than about 3% w/w of the lyophilized cake. Any of the lyophilized cakes may further comprise a pH modifier, such as a mineral acid, preferably phosphoric acid, preferably in an amount sufficient to adjust the pH to about 7 or lower, such as about 6 or lower, preferably about 1 to 6, more preferably about 2 to 5, more preferably about 4 or lower, more preferably about 3 to 4, more preferably about 4.

A particular advantage of the lyophilized cakes of the present invention is that they are readily reconstituted to form clear, near-colorless to colorless solutions that are free of discoloration (i.e., are colorless or near colorless) and/or particulate matter, suitable for injection into humans in about 180 seconds or less. Preferably, the lyophilized cakes of the present invention are readily reconstituted to form clear, colorless solutions that are free of particulate matter, suitable for injection into humans in about 180 seconds or less. In certain preferred embodiments, the lyophilized cakes are reconstituted in about 120 seconds or less to form clear, colorless solutions that are free of particulate matter, suitable for injection into humans. Preferably, the lyophilized cakes are reconstituted in about 90 seconds or less to form clear, colorless solutions that are free of particulate matter, suitable for injection into humans. More preferably, the lyophilized cakes are reconstituted in about 60 seconds or less to form clear, colorless solutions that are free of particulate matter, suitable for injection into humans. More preferably, the lyophilized cakes are reconstituted in about 30 seconds or less to form clear, colorless solutions that are free of particulate matter, suitable for injection into humans. More preferably, the lyophilized cakes are reconstituted in about 10 seconds or less to form clear, colorless solutions that are free of particulate matter, suitable for injection into humans.

Another advantage of the lyophilized cakes of the present invention is that they exhibit highly desirable storage stability profiles. Storage conditions can vary and can include variations in temperature, for example, from about 5° C. to about 40° C., and variations in relative humidity (RH), for example from about 10% RH to about 75% RH. For the purposes of the present application, 5° C.+/−3° C. and ambient RH are referred to as "refrigerated conditions," 25° C.+/−2° C. and 60% RH+/−5% RH are referred to as "room temperature conditions," 30° C.+/−2° C. and 65% RH+/−5% RH are referred to as "enhanced room temperature conditions," and 40° C.+/−2° C. and 75% RH+/−5% RH are referred to as "accelerated conditions." Storage conditions can also include variations in storage time. For example, lyophilized cakes of the present invention can be stored for about 1 month, about 2 months, about 3 months, about 6 months, about 1 year, or more. Analysis of the lyophilized cakes can be performed using any technique known in the art, for example, HPLC, GC, and the like.

Preferably, the lyophilized cakes of the present invention contain less than about 5% w/w, more preferably, less than about 3% w/w, of degradation impurities after storage of the cake for six months under refrigerated conditions. By "degradation impurities" is meant impurities in the cake as a result of decomposition of the drug during storage (i.e., drug decomposition that takes place after the lyophilized cake is formed). In other words, degradation impurities do not include impurities present in the cake at the time of its initial production (e.g., impurities present in the drug prior to lyophilization or impurities arising during the lyophilization process). Preferably, the lyophilized cakes of the present invention contain less than about 2% w/w, more preferably, less than about 1% w/w, of degradation impurities after storage of the cake for six months under refrigerated conditions. More preferably, the lyophilized cakes of the present invention contain no more than about 0.5% w/w, more preferably, no more than about 0.2% w/w, most preferably, no more than about 0.1% w/w, of degradation impurities after storage of the cake for six months under refrigerated conditions. Preferably, the lyophilized cakes of the present invention contain less than about 5% w/w, more preferably, less than about 3% w/w, of degradation impurities after storage of the cake for six months under room temperature conditions. Preferably, the lyophilized cakes of the present invention contain less than about 2% w/w, more preferably, less than about 1% w/w, of degradation impurities after storage of the cake for six months under room temperature conditions. More preferably, the lyophilized cakes of the present invention contain no more than about 0.5% w/w, more preferably, no more than about 0.2% w/w, most preferably, no more than about 0.1% w/w, of degradation impurities after storage of the cake for six months under room temperature conditions. Preferably, the lyophilized cakes of the present invention contain less than about 5% w/w, more preferably, less than about 3% w/w, of degradation impurities after storage of the cake for six months under enhanced room temperature conditions. Preferably, the lyophilized cakes of the present invention contain less than about 2% w/w, more preferably, less than about 1% w/w, of degradation impurities after storage of the cake for six months under enhanced room temperature conditions. More preferably, the lyophilized cakes of the present invention contain no more than about 0.5% w/w, more preferably, no more than about 0.2% w/w, most preferably, no more than about 0.1% w/w, of degradation impurities after storage of the cake for six months under enhanced room temperature conditions. Preferably, the lyophilized cakes of the present invention contain less than about 5% w/w, more preferably, less than about 3% w/w, of degradation impurities after storage of the cake for three months under accelerated conditions. Preferably, the lyophilized cakes of the present invention contain less than about 2% w/w, more preferably, less than about 1% w/w, of degradation impurities after storage of the cake for three months under accelerated conditions. More preferably, the lyophilized cakes of the present invention contain no more than about 0.5% w/w, more preferably, no more than about 0.2% w/w, most preferably, no more than about 0.1% w/w, of degradation impurities after storage of the cake for three months under accelerated conditions. Preferably, the lyophilized cakes of the present invention contain less than about 5% w/w, more preferably, less than about 3% w/w, of degradation impurities after storage of the cake for six months under accelerated conditions. Preferably, the lyophilized cakes of the present invention contain less than about 2% w/w, more preferably, less than about 1% w/w, of degradation impurities after storage of the cake for six months under accelerated conditions. More preferably, the lyophilized cakes of the present invention contain no more than about 0.5% w/w, more preferably, no more than about 0.2% w/w, most preferably, no more than about 0.1% w/w, of degradation impurities after storage of the cake for six months under accelerated conditions. Analysis of the claimed cakes can be performed using any technique known in the art, for example, HPLC, GC, and the like. The content of degradation impurities in a sample can be determined by calculating the total relative area of the impurity peaks in the HPLC chromatogram of the sample compared to the total area of all peaks in the chromatogram (e.g., [total peak area of impurities]/[total peak area of sample]×100%) at time zero and after storage, and then subtracting the time zero impurities from the impurities after storage (e.g., [impurities after storage]−[initial impurities]=degradation impurities).

Preferably, the lyophilized cakes of the present invention contain less than about 5% w/w, more preferably, less than about 3% w/w, of degradation impurities after storage of the cake for twelve months under refrigerated conditions. Preferably, the lyophilized cakes of the present invention contain less than about 2% w/w, more preferably, less than about 1% w/w, of degradation impurities after storage of the cake for twelve months under refrigerated conditions. More preferably, the lyophilized cakes of the present invention contain no more than about 0.5% w/w, more preferably, no more than about 0.2% w/w, most preferably, no more than about 0.1% w/w, of degradation impurities after storage of the cake for twelve months under refrigerated conditions. Preferably, the lyophilized cakes of the present invention contain less than about 5% w/w, more preferably, less than about 3% w/w, of degradation impurities after storage of the cake for twelve months under room temperature conditions. Preferably, the lyophilized cakes of the present invention contain less than about 2% w/w, more preferably, less than about 1% w/w, of degradation impurities after storage of the cake for twelve months under room temperature conditions. More preferably, the lyophilized cakes of the present invention contain no more than about 0.5% w/w, more preferably, no more than about 0.2% w/w, most preferably, no more than about 0.1% w/w, of degradation impurities after storage of the cake for twelve months under room temperature conditions. Preferably, the lyophilized cakes of the present invention contain less than about 5% w/w, more preferably, less than about 3% w/w, of degradation impurities after storage of the cake for twelve months under enhanced room temperature conditions. Preferably, the lyophilized cakes of the present invention contain less than about 2% w/w, more preferably, less than about 1% w/w, of degradation impurities after storage of the cake for twelve months under enhanced room temperature conditions. More preferably, the lyophilized cakes of the present invention contain no more than about 0.5% w/w, more preferably, no more than about 0.2% w/w, most preferably, no more than about 0.1% w/w, of degradation impurities after storage of the cake for twelve months under enhanced room temperature conditions. Preferably, the lyophilized cakes of the present invention contain less than about 5% w/w, more preferably, less than about 3% w/w, of degradation impurities after storage of the cake for twelve months under accelerated conditions. Preferably, the lyophilized cakes of the present invention contain less than about 2% w/w, more preferably, less than about 1% w/w, of degradation impurities after storage of the cake for twelve months under accelerated conditions. More preferably, the lyophilized cakes of the present invention contain no more than about 0.5% w/w, more preferably, no more than about 0.2% w/w, most preferably, no more than about 0.1% w/w, of degradation impurities after storage of the cake for twelve months under accelerated conditions.

Preferably, the lyophilized cakes of the present invention contain no more than about 1% w/w of any individual degradation impurity after storage of the cake for six months under refrigerated conditions. Preferably, the lyophilized cakes of the present invention contain no more than about 1% w/w of any individual degradation impurity after storage of the cake for six months under room temperature conditions. Preferably, the lyophilized cakes of the present invention contain no more than about 1% w/w of any individual degradation impurity after storage of the cake for six months under enhanced room temperature conditions. Preferably, the lyophilized cakes of the present invention contain no more than about 1% w/w of any individual degradation impurity after storage of the cake for three months under accelerated conditions. Preferably, the lyophilized cakes of the present invention contain no more than about 1% w/w of any individual degradation impurity after storage of the cake for six months under accelerated conditions. The content of any individual degradation impurity in a sample can be determined by calculating the relative area of the impurity peak in the HPLC chromatogram of the sample compared to the total area of all peaks in the chromatogram (e.g., [peak area of individual degradation impurity]/[total peak area of sample]–100%) at time zero and after storage, and then subtracting the time zero content of the impurity from the content of that impurity after storage (e.g., [content of individual impurity after storage]–[initial content of individual impurity]=content of individual degradation impurity).

Preferably, the lyophilized cakes of the present invention contain no more than about 0.5% w/w of any individual degradation impurity after storage of the cake for six months under refrigerated conditions. More preferably, the lyophilized cakes of the present invention contain no more than about 0.2% w/w, more preferably no more than about 0.1%, of any individual degradation impurity after storage of the cake for six months under refrigerated conditions. Preferably, the lyophilized cakes of the present invention contain no more than about 0.5% w/w of any individual degradation impurity after storage of the cake for six months under room temperature conditions. More preferably, the lyophilized cakes of the present invention contain no more than about 0.2% w/w, more preferably no more than about 0.1%, of any individual degradation impurity after storage of the cake for six months under room temperature conditions. Preferably, the lyophilized cakes of the present invention contain no more than about 0.5% w/w of any individual degradation impurity after storage of the cake for six months under enhanced room temperature conditions. More preferably, the lyophilized cakes of the present invention contain no more than about 0.2% w/w, more preferably no more than about 0.1%, of any individual degradation impurity after storage of the cake for six months under enhanced room temperature conditions. Preferably, the lyophilized cakes of the present invention contain no more than about 0.5% w/w of any individual degradation impurity after storage of the cake for three months under accelerated conditions. More preferably, the lyophilized cakes of the present invention contain no more than about 0.2% w/w, more preferably no more than about 0.1%, of any individual degradation impurity after storage of the cake for three months under accelerated conditions. Preferably, the lyophilized cakes of the present invention contain no more than about 0.5% w/w of any individual degradation impurity after storage of the cake for six months under accelerated conditions. More preferably, the lyophilized cakes of the present invention contain no more than about 0.2% w/w, more preferably no more than about 0.1%, of any individual degradation impurity after storage of the cake for six months under accelerated conditions.

Preferably, the lyophilized cakes of the present invention contain no more than about 0.5% w/w of any individual degradation impurity after storage of the cake for twelve months under refrigerated conditions. More preferably, the lyophilized cakes of the present invention contain no more than about 0.2% w/w, more preferably no more than about 0.1%, of any individual degradation impurity after storage of the cake for twelve months under refrigerated conditions. Preferably, the lyophilized cakes of the present invention contain no more than about 0.5% w/w of any individual degradation impurity after storage of the cake for twelve months under room temperature conditions. More preferably, the lyophilized cakes of the present invention contain no more than about 0.2% w/w, more preferably no more than about 0.1%, of any individual degradation impurity after storage of the cake for twelve months under room temperature conditions. Preferably, the lyophilized cakes of the present invention contain no more than about 0.5% w/w of any individual degradation impurity after storage of the cake for twelve months under enhanced room temperature conditions. More preferably, the lyophilized cakes of the present invention contain no more than about 0.2% w/w, more preferably no more than about 0.1%, of any individual degradation impurity after storage of the cake for twelve months under enhanced room temperature conditions. Preferably, the lyophilized cakes of the present invention contain no more than about 0.5% w/w of any individual degradation impurity after storage of the cake for twelve months under accelerated conditions. More preferably, the lyophilized cakes of the present invention contain no more than about 0.2% w/w, more preferably no more than about 0.1%, of any individual degradation impurity after storage of the cake for twelve months under accelerated conditions.

Preferably, the lyophilized cakes of the present invention exhibit a decrease in drug purity of no more than about 2%, preferably no more than about 1%, after storage of the cake for six months under refrigerated conditions. Preferably, the lyophilized cakes of the present invention exhibit a decrease in drug purity of no more than about 2%, preferably no more than about 1%, after storage of the cake for six months under room temperature conditions. Preferably, the lyophilized cakes of the present invention exhibit a decrease in drug purity of no more than about 2%, preferably no more than about 1%, after storage of the cake for three months under accelerated conditions. Preferably, the lyophilized cakes of the present invention exhibit a decrease in drug purity of no more than about 2%, preferably no more than about 1%, after storage of the cake for six months under accelerated conditions. The purity of the drug in a sample can be determined from the relative area of the drug peak in the HPLC chromatogram of the sample as compared to the total area of all peaks in the chromatogram (e.g., [peak area of drug]/[total peak area of sample]×100%), and the decrease in purity can be calculated as [initial purity]−[purity after storage]=decrease in drug purity.

Preferably, the lyophilized cakes of the present invention exhibit a decrease in drug purity of no more than about 0.5% after storage of the cake for six months under refrigerated conditions. Preferably, the lyophilized cakes of the present invention exhibit a decrease in drug purity of no more than about 0.5% after storage of the cake for six months under room temperature conditions. Preferably, the lyophilized cakes of the present invention exhibit a decrease in drug purity of no more than about 0.5% after storage of the cake for three months under accelerated conditions. Preferably, the lyophilized cakes of the present invention exhibit a decrease in drug purity of no more than about 0.5% after storage of the cake for six months under accelerated conditions.

Lyophilized cakes of the invention may be prepared using any of the techniques known to those skilled in the art. In those embodiments of the invention comprising a compound of Formula I or II or a pharmaceutically acceptable salt or ester thereof, a cyclodextrin, a bulking agent, and a surfactant, one preferred method includes preparing a first mixture comprising the cyclodextrin, the bulking agent, and water. Preferred first mixtures include hydroxypropyl β cyclodextrin as the cyclodextrin and mannitol as the bulking agent. A portion of this first mixture is mixed with the surfactant, preferably polysorbate 20, to form a second mixture. The compound of Formula I or Formula II or a pharmaceutically acceptable salt or ester thereof, preferably Compound 1 or bortezomib, is combined with the second mixture to form a drug mixture. In some embodiments, an organic solvent, preferably tert-butanol, can be added to either the first mixture or the drug mixture, or both. The remainder of the first mixture is then mixed with the drug mixtures to form a pre-lyophilization solution. In some embodiments, the pre-lyophilization solution is sterilized using techniques known in the art, for example, sterile filtration. The pre-lyophilization solution is then lyophilized using lyophilization techniques known in the art.

In another embodiment, the cyclodextrin, preferably hydroxypropyl β cyclodextrin is combined with water to form a first mixture. The compound of Formula I or II or a pharmaceutically acceptable salt or ester thereof, preferably Compound 1 or bortezomib, is combined with a surfactant to form a drug mixture. In some embodiments, an organic solvent, preferably tert-butanol, is added to the first mixture, the drug mixture, or both. The first mixture and the drug mixture are combined to form a pre-lyophilization solution. In some embodiments, the pre-lyophilization solution is sterilized using techniques known in the art, for example, sterile filtration. The pre-lyophilization solution is then lyophilized using lyophilization techniques known in the art.

In those embodiments of the invention comprising a compound of Formula I or II or a pharmaceutically acceptable salt or ester thereof, a cyclodextrin, and a bulking agent, one preferred method includes preparing a first mixture containing the cyclodextrin, the bulking agent, and water. Preferred first mixtures include hydroxypropyl β cyclodextrin as the cyclodextrin and mannitol as the bulking agent. A drug mixture containing the compound of Formula I or Formula II or a pharmaceutically acceptable salt or ester thereof, preferably Compound 1 or bortezomib, and an organic solvent, preferably tert-butanol, is prepared. The first mixture and the drug mixture are combined to provide a pre-lyophilization solution. In some embodiments, the pre-lyophilization solution is sterilized using techniques known in the art, for example, sterile filtration. The pre-lyophilization solution is then lyophilized using lyophilization techniques known in the art.

In each of the above embodiments, the pH can be adjusted with a pH modifier at any time prior to lyophilization. Preferably, a pH modifier is added to the pre-lyophilization solution to adjust the pH.

The invention provides a method for manufacturing a lyophilized cake, comprising the step of lyophilizing a mixture containing (a) a drug chosen from a compound of Formula I, Formula II, or a pharmaceutically acceptable salt or ester thereof:

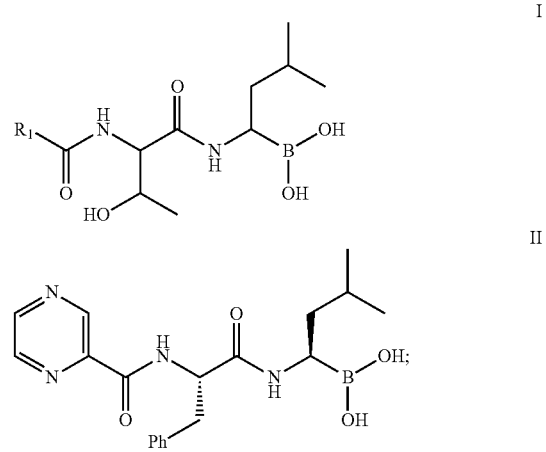

wherein $R_1$ is an optionally substituted 5-, 6-, or 10-membered heteroaryl having at least one N or $R_1$ is an optionally substituted 6- or 10-membered aryl;

(b) a cyclodextrin; and (c) at least one member selected from the group consisting of bulking agents and surfactants. Preferred drugs, cyclodextrins, bulking agents, surfactants, and other ingredients are as previously described.

It is envisioned that the lyophilized cakes of the present invention can be used in the treatment of cancer. For examples, the lyophilized cakes of the present invention can be used to treat chronic lymphocytic leukemia, Hodgkin's disease, non-Hodgkin's lymphoma, multiple myeloma or breast cancer. Preferably, the lyophilized cake is used to treat multiple myloma.

In most instances, the lyophilized cake of the present invention is administered by reconstituting the cake (e.g., with sterile Water for Injection, 0.9% NaCl, or 5% mannitol) and injecting the resulting solution. However, the lyophilized cake is also suitable for oral administration, optionally in admixture with other excipients.

It is envisioned that in some embodiments of the present invention, the described lyophilized cakes can be administered, either serially or simultaneously, with another antineoplastic agent. There are large numbers of antineoplastic agents available in commercial use, in clinical evaluation and in pre-clinical development, which could be selected for treatment of neoplasia by combination drug chemotherapy. Such antineoplastic agents fall into several major categories, namely, antibiotic-type agents, covalent DNA-binding drugs, antimetabolite agents, hormonal agents, including glucocorticoids such as prednisone and dexamethasone, immunological agents, interferon-type agents, differentiating agents such as the retinoids, pro-apoptotic agents, and a category of miscellaneous agents, including compounds such as antisense, small interfering RNA, and the like. Alternatively, other antineoplastic agents, such as metallomatrix proteases (MMP) inhibitors, SOD mimics or alpha$_v$beta$_3$ inhibitors may be used.

The following examples are offered for illustrative purposes, and are not intended to limit the invention in any manner Those of skill in the art will readily recognize a variety of noncritical parameters which can be changed or modified to yield essentially the same results.

EXAMPLES

HPLC analysis can be performed using, for example, a Thermo BetaBasic C18 (150 mm×4.6 mm ID, 5 μm) column or a Waters Symmetry C18 (150 mm×4.6 mm, 3.5 μm) column at 35° C. using 254 nm UV detection with a flow rate of 1 mL/min, an injection volume of 8 μL or 10 μL, and a total run time of 42 min (run time=35 min, re-equilibrium time=7 min) The following gradient mobile phase is a preferred gradient system:

| Time (min) | TFA 0.05% in deionized water (%) | TFA 0.05% in Acetonitrile (%) |
|---|---|---|
| 0 | 75 | 25 |
| 2 | 75 | 25 |
| 17 | 65 | 35 |
| 30 | 10 | 90 |
| 35 | 10 | 90 |
| 35.1 | 75 | 25 |
| 42 | 75 | 25 |

Percent purities can be calculated using methods known in the art. For example, the purity of Compound 1, as determined using HPLC, can be calculated as follows:

([Area of Compound 1]÷[total area of injected sample])×100%=Compound 1 purity %

Samples for HPLC analysis can be prepared by, for example, reconstituting the lyophilized cake of the invention using about 4 mL of DI (deionized) water or SWFI (sterile water for injection). After adding the water, each vial is shaken or sonicated for about 10 seconds, or until all solids have dissolved. Approximately 1 mL of the reconstituted solution can be removed and placed in an HPLC vial for analysis.

Preparation 1. Preparation of (1R)-1-[(3aS,4S,6S,7aR)-hexahydro-3a,5,5-trimethyl-4,6-methano-1,3,2-benzodioxaborol-2-yl]-3-methylbutylamine hydrochloride salt A 20 liter Chemglass® jacketed reactor equipped with overhead stirring, nitrogen sweep, thermocouple with temperature readout, a 1 liter addition funnel, sub-surface gas dispersion tube and auxiliary heater/chiller was charged with 8.0 liters of anhydrous methyl tert-butyl ether. The chiller was set to −40° C. The solvent was cooled to −31.3° C. with agitation. Next, 714.4 g (19.71 mol, 5.0 eq) of HCl (g) was added subsurface over 1.75 hours while maintaining the temperature between −25.7 and −10.0° C. Next, 1.6235 kg (3.964 mol) of N,N-Bis(trimethylsilyl)-(1R)-1-[(3aS,4S,6S,7aR)-hexahydro-3a,5,5-trimethyl-4,6-methano-1,3,2-benzodioxaborol-2-yl]-3-methylbutylamine (obtained by a method similar to that disclosed in U.S. Patent Publication No. 2005/0240047 (Pickersgill et al.), was dissolved in 2.1 liters of methyl tert-butyl ether. Next, the solution was added to the HCl solution over 40 minutes while maintaining the reaction temperature between −25 and −10° C. After addition was complete the reaction was warmed to ambient temperature and the chiller was turned off The reaction was allowed to warm to ambient temperature and was stirred overnight. GC analysis the next morning indicated that the reaction was complete. Next, the reaction was concentrated on the rotary evaporator to a volume of 1-2 liters. 3 liters of heptanes were added to the mixture and the distillation continued to remove 3 more liters of distillate. Next, 6 more liters of heptanes were added portion wise while removing 1 more liter of distillate. The product mixture was transferred to the 20 liter Chemglass® jacketed reactor equipped as previously described and allowed to slowly stir overnight at ambient temperature. The next morning the mixture was cooled to −15 and −10° C. and allowed to agitate for 1 hour. The product was filtered through a medium glass sintered filter funnel equipped with a #1 Whatman® filter paper. The product cake was washed with 2 liters of cold (0° C.) heptane and dried in an oven under vacuum (29 mmHg) at 35° C. and purged with nitrogen. The yield was 996.0 g (84%) with a purity of 93.9 A %, and a diastereomer ratio of 98.75:1.25 (d.e.=97.5%).

Preparation 2. Preparation of 6-(2S,3R)-N-[(1R)-1-(1,3,6,2-dioxazaborocan-2-yl)-3-methylbutyl}-3-hydroxy-2-{(6-phenylpyridin-2-yl)formamido]butanamide (i.e., Compound 10)

Step A. Preparation of 6-Phenyl-pyridine-2-carbonyl chloride

A 2-L three neck round bottomed flask equipped with an overhead stirrer, thermocouple, heating mantle with digital temperature controller, condenser and nitrogen inlet/outlet was charged with 100.0 g (0.502 mol) of 6-phenyl-2-pyridinecarboxylic acid and 1500 mL of toluene (Kf<0.02 wt %) then warmed to 40° C. Thionyl chloride (110 mL; 1.51 mol, 3 eq) was then added to the thin slurry via addition funnel over 20 minutes. The thin slurry was heated to 75° C. and stirred overnight (typically 10-16 hr), until it became a clear solution. Reaction was assayed via HPLC for conversion as the methyl ester derivative. After cooling the reaction mixture to room temperature the solvent and excess thionyl chloride were removed in vacuo as follows: Reaction mixture was stripped under full vacuum at 40° C. (bath temperature) to approximately ⅓ its original volume (~500 ml) and then (1000 ml) of fresh toluene was added. Concentration was continued, again stripping to ⅓ original volume (~500 ml) followed by re-dilution with 1000 ml of fresh toluene. The total amount of toluene removed was ~2000 mL.

Step B. Preparation of (2S,3R)-3-Hydroxy-2-[oxo-2-(6-phenyl-pyridin-2-yl)-ethyl}-butyric acid A 3-L three neck round bottomed flask was equipped with an overhead stirrer, thermocouple, pressure equalizing dropping funnel, nitrogen inlet/outlet and ice/water cooling bath. L-threonine, 62.8 g (0.53 mol) was added, followed by 117 g (1.1 mol) of sodium carbonate and 1500 mL of deionized water. The aqueous solution was cooled to 10.0° C. During this time the addition funnel was charged with the acid chloride/toluene solution prepared in Step A. This toluene solution was added dropwise to the aqueous reaction over approximately 10 minutes at ~10° C. Once the addition was complete, the reaction was warmed to room temperature (~22-25° C.) and vigorously stirred until it was shown to be complete by HPLC analysis (typically ~3 hr). The reaction mixture was then transferred to a separatory funnel and the two layers were separated. The lower aqueous phase was then recharged to the reaction flask. Methanol (800 mL) was then added to the mixture followed by pH adjustment (target pH=1-2) with 2.5M HCl (~850 mL), keeping the temperature at 15-20° C. Some off-gassing occurred at ~pH=5, followed by precipitation of the product at pH=3. The slurry was allowed to stir at room temperature for 30 minutes post pH adjustment. The white solid was collected by vacuum filtration, (mother liquor losses<2 mg/mL), washed with deionized water (2×500 ml) then dried in a vacuum oven at 40° C. with a nitrogen sweep to a constant weight to provide 141 g (0.471 mol, 94%) of the title compound with an HPLC purity of 99 A % (95 wt %). $^1$H NMR (d6-DMSO, 400 MHz) δ 12.9 (s, 1H, b), 8.71 (d, 1H, J=9.16 Hz), 8.23 (d, 1H, J=7.24 Hz), 8.1 (m, 3H), 8.03 (d, 1H, J=7.0 Hz), 7.55 (m, 3H), 5.34 (s, 1H, b), 4.46 (dd, 1H, J=2.52, 9.16 Hz), 4.34 (dd, 1H, J=1.92, 6.24 Hz), 1.15 (d, 3H, J=6.4 Hz).

Step C. Preparation of N-[(1S,2R)-1[[[(1R)-1-1 [(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide A 10 liter jacketed reaction vessel equipped with a thermocouple, stirring shaft with impeller, addition funnel, and low temperature recirculating bath was charged with 156.1 g (0.52 mol, 1.0 eq) of (2S,3R)-3-Hydroxy-2-[oxo-2-(6-phenyl-pyridin-2-yl)-ethyl}-butyric acid (produced as in Step B), 218.8 g (0.575 mol, 1.1 eq) of O-(7-azabenzotriazol-1-yl)-N,N,N'N'-tetramethyluronium hexafluorophosphate (HATU), 157.7 g (0.522 mol, 1.0 eq) of (1R)-1-[(3aS,4S,6S,7aR)-hexahydro-3a,5,5-trimethyl-4,6-methano-1,3,2-benzodioxaborol-2-yl]-3-methylbutylamine hydrochloride salt (produced as in Preparation 1) (98.8:1.2 mixture of isobutyl diastereomers (R:S))], and 2355 mL of N,N-dimethylformamide (DMF). Agitation was begun and the solids dissolved before cooling the reaction mixture to <−25.0° C. Diisopropylethylamine (218.6 mL, 162.2 g, 1.25 mol, 2.4 eq) was charged to the addition funnel and then added dropwise to the reaction mixture over 30~ minutes at −25° C. to −30° C. Once addition was complete the reaction was stirred at −30° C. for six hours. In a separate twenty-two liter four-neck reaction flask equipped with an overhead stirrer and thermocouple was charged 3925 mL of DI water and 3925 mL of ethyl acetate. The reaction mixture was transferred to this flask over five minutes at RT. The lower aqueous layer was separated and discarded. A solution of 393 g of sodium phosphate monobasic, monohydrate in 3925 mL of DI water was prepared and the organic phase was washed with this solution. The lower aqueous phase was again removed and discarded. A solution of 376.9 g of sodium bicarbonate in 4710 mL of DI water was prepared and the organic phase was washed with this solution which had been split into two portions. Once again the lower aqueous phase was separated and discarded. A saturated sodium chloride solution was prepared using 481.4 g of sodium chloride in 3140 mL of DI water and the organic phase was washed with this solution, the layers were separated and the lower aqueous phase discarded. Norit GAC 1240+ carbon (157 g) was added to the organic phase and the suspension was stirred at RT overnight (13.8 hours). The carbon was removed by vacuum filtration through Whatman GF/C glass fiber filter paper, then washed with 350 mL of ethyl acetate. The filtrate was concentrated to a foam on a rotary evaporator at under vacuum with a 33-44° C. bath temperature to provide 231.5 g (0.422 mol, 80.9%) of the title compound as a foam with a chemical purity of 96.4%. The level of threonine isomer was 1.16 A %. %. $^1$H NMR (d6-DMSO, 400 MHz) δ 8.98 (d, b, 1H, J=2.99 Hz), 8.76 (d, 1H, J=8.55 Hz), 8.2 (m, 3H), 8.11 (t, 1H, J=7.71 Hz), 8.02 (d, 1H, J=7.54 Hz), 7.54 (m, 3H), 5.26 (d, 1H, J=4.95 Hz), 4.49 (dd, 1H, J=4.22, 8.52 Hz), 4.13 (m, 2H), 2.6 (m, b, 1H), 2.19 (m, b, 1H), 2.02 (m, b, 1H), 1.83 (t, 1H, J=5.38 Hz), 1.75 (s, b, 1H), 1.68 (m, b, 1H), 1.62 (d, 1H, J=13.9 Hz), 1.36 (d, 1H, J=10.05 Hz), 1.3 (m, b, 3H), 1.22 (d, 6H, J=11.65 Hz), 1.12 (d, 3H, J=6.26 Hz), 0.84 (d, 6H, J=6.57 Hz), 0.79 (s, 3H).

Step D. Preparation of 6-(2S,3R)-N-[(1R)-1-(1,3,6,2-dioxazaborocan-2-yl}-3-methylbutyl}-3-hydroxy-2-{ (6-phenylpyridin-2-yl)formamido]butanamide (i.e., Compound 10)

Option 1—Two Step Procedure:

A twelve liter four neck round bottom flask was equipped with an overhead stirrer, thermocouple and nitrogen outlet before being charged with a solution of 229.8 g (0.42 mol, 1 eq) of N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide (produced as in Step C) in 2310 mL of methanol. To this was added 3465 mL of n-heptane, 108 g (1.06 mol, 2.5 eq) of (2-methylpropyl)boronic acid and a solution of 70 mL (84 g, 0.85 mol, 2.0 eq) of 37% hydrochloric acid in 353 mL of DI water. Agitation was begun and the two phase mixture was stirred at RT for 16 hours. The reaction mixture was transferred in portions to a four liter separatory funnel and the lower methanolic phase was separated and returned to the reaction flask. The upper heptane layer was discarded. A fresh charge of 3465 mL of n-heptane was added to the reaction and the reaction was agitated at RT for an additional two hours. Agitation was stopped and the phases were separated and the lower methanolic layer was extracted with n-heptane (2×4600 mL). The heptane phases were discarded and the methanolic phase was concentrated in vacuo with a bath temperature of 40° C. Ethyl acetate (4620 mL) was charged to the evaporation flask and the sticky yellow residue was dissolved before transferring to a twelve-liter reaction flask. A solution of 665.4 g of sodium bicarbonate in 7650 mL of DI water was prepared and used to wash the ethyl acetate layer in two portions (1×4000 mL and 1×3850 mL). A solution of 1059.7 g of sodium chloride in 2700 mL of DI water was prepared and then used to wash the ethyl acetate phase.

After separation of layers the ethyl acetate layer was treated with 47.3 g (0.45 mol, 1.1 eq) of diethanolamine The mixture was allowed to stir at RT overnight. Precipitated solids were collected by vacuum filtration using a closed filtration flask and the wet cake was washed with 500 mL of ethyl acetate. The sealed filter funnel was transferred to a glove box where it was opened and the 481.8 g of wet cake was transferred to two pyrex drying trays which were then placed into a vacuum oven. The product was dried to a constant weight at 23.5 in of Hg and 50° C. over 27 hours to provide 179.7 g (0.372 mol, 88.8%) of the title compound with a chemical purity of 98.6% and a chiral purity of 98.8% de. $^1$H NMR (d6-DMSO, 400 MHz) δ 8.8 (d, 1H, J=8.52 Hz), 8.2 (m, 3H), 8.1 (t, 1H, J=7.68 Hz), 8.0 (dd, 1H, J=6.7, 0.9 Hz), 7.5 (m, 3H), 7.2 (d, 1H), 6.5 (t,b, 1H), 5.1 (d, 1H, J=4.92 Hz), 4.5 (dd, 1H), 4.2 (m, 1H), 3.6 (m, 2H), 3.5 (m, 2H), 3.1 (m, 1H), 3.0 (m, 2H), 2.7 (m, 2H), 1.6 (m, 1H), 1.3 (m, 1H), 1.2 (m, 1H), 1.1 (d, 3H, J=6.32 Hz), 0.8 (2d, 6H, J=6.68, 6.52 Hz).

Option 2—One Step Procedure:

A 50 mL three neck round bottom flask was equipped with a thermocouple, stir bar, nitrogen inlet/outlet, heating mantle and temperature controller. The flask was charged with 2.0 g (3.65 mmol, 1.0 eq) of N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide (produced as in Step C) and 20 mL of MTBE. The reaction mixture was stirred for approximately 10 minutes until all the solids dissolved. Diethanolamine (0.44 mL, 0.48 g, 4.57 mmol, 1.25 eq) was charged via syringe, along with 2 drops of methanesulfonic acid, to the light yellow solution and the mixture was heated to 50° C. After approximately 30 minutes a white precipitate began to form. Stirring was continued overnight before cooling to room temperature. The solids were collected by vacuum filtration, washed with MTBE (1×20 mL) then dried under vacuum at 60° C. overnight to give 0.92 g (1.9 mmol, 52%) of the title compound as a white solid with a chemical purity of 91.9% and a chiral purity of >99.5% de.

Step E (Optional). Purification of 6-(2S,3R)-N-[(1R)-1-(1,3,6,2-dioxazaborocan-2-yl)-3-methylbutyl}-3-hydroxy-2-{(6-phenylpyridin-2-yl)formamido]butanamide (i.e., Compound 10)

A two liter four neck round bottom flask was equipped with an overhead stirrer, thermocouple, condenser, heating mantle, temperature controller and nitrogen outlet before being charged with 175 g (0.363 mol) of 6-(2S,3R)-N-[(1R)-1-(1,3,6,2-dioxazaborocan-2-yl)-3-methylbutyl}-3-hydroxy-2-{(6-phenylpyridin-2-yl)formamido]butanamide (produced as in Step D) and 1400 mL (8 volumes) of 95% ethanol. Agitation was begun and the resultant suspension was heated to 75.7° C. over 21 minutes. Once at temperature the solution was stirred for 80 minutes at 74.9-75.8° C. before cooling to 2.7° C. over 80 minutes. The reaction slurry was then stirred at 2.2-6.0° C. overnight (17 hours) to fully crystallize the product. Precipitated solids were collected by vacuum filtration using a closed filtration flask and the wet cake was washed with 350 mL of 95% ethanol. The sealed filter funnel was transferred to a glove box where it was opened and the 203.8 g of wet cake was transferred to a pyrex drying tray which was then placed into a vacuum oven. The product was dried to a constant weight at 23.5 in of Hg and 50° C. over 19 hours to provide 147.3 g (0.306, mol, 84.2%) of the title compound with a chemical purity of 99.76% and an optical purity of >99.8% de.

Preparation 3. Preparation of [(1R)-1-[[(2S,3R)-3-Hydroxy-2-[[(6-phenylpyridin-2-yl)carbonyl]amino]-1-oxobutyl]amino]-3-methylbutyl]boronic acid (i.e., Compound 1)

A 50 mL three neck round bottom flask equipped with a thermocouple, stir bar and nitrogen outlet was charged with 1.65 g (3.4 mmol) of Compound 10 (chemical purity=99.5%, chiral purity>99.5% de), 17 mL of methyl isobutyl ketone and 1.7 mL of 2N hydrochloric acid. The mixture was stirred overnight. The layers of the reaction were separated and the organic layer was dried over magnesium sulfate, filtered and evaporated to dryness in vacuo. The residue was triturated in pentane and the resultant white solid was collected by vacuum filtration before drying in a vacuum oven overnight at 60° C. to give 1.26 g (3.1 mmol, 90%) of the title compound. HPLC indicates a purity of 99.6 A %. Chiral purity>99.5% de. $^1$H NMR (d4-MeOD, 400 MHz) δ 8.17 (m, 2H), 8.13 (m, 1H), 8.05 (m, 2H), 7.5 (m, 3H), 4.75 (d, 1H, J=3.04 Hz), 4.42 (dq, 1H, J=2.92, 6.4), 2.7 (t, b, 1H), 1.61 (m, 1H), 1.35 (t, 2H, J=7.48 Hz), 1.29 (d, 3H, J=6.36 Hz), 0.89 (d, 6H, J=6.52 Hz).

Preparation 4. Preparation of (2S)-N-[(1R)-1-(1,3,6,2-dioxazaborocan-2-yl)-3-methylbutyl]-3-phenyl-2-(pyrazin-2-ylformamido)propanamide (i.e., Compound 13)

Step A. Preparation of Pyrazine-2-carbonyl chloride

A 500 ml three neck round bottomed flask equipped with a stir bar, thermocouple, heating mantle with digital temperature controller, condenser and nitrogen inlet/outlet was charged with 15 g (0.12 mol) of pyrazine carboxylic acid, 225 mL of toluene (Kf<0.02 wt %) and 26.4 ml (43 g, 0.36 mol) of thionyl chloride. The thin slurry was heated to 75° C. and stirred overnight (10-16 hr). After cooling the reaction mixture to room temperature the solvent and excess thionyl chloride were removed in vacuo as follows: Reaction mixture was stripped under full vacuum at 60° C. (bath temperature) to approximately ⅓ its original volume and then (175 ml) of fresh toluene was added. Concentration was continued, again stripping to ⅓ original volume followed by re-dilution with 225 ml of fresh toluene to provide the pyrazine acid chloride in a toluene solution.

Step B. Preparation of (S)-3-Phenyl-2-[(pyrazine-2-carbonyl)-amino]-propionic acid A second 500 ml three neck round bottomed flask was equipped with a stir bar, thermocouple, pressure equalizing dropping funnel, nitrogen inlet/outlet and ice/water cooling bath. L-Phenylalanine, 20.2 g (0.122 mol) was added, followed by 28.2 g (0.266 mol) of sodium carbonate and 225 mL of deionized water. The aqueous solution was cooled to 10.0° C. During this time the addition funnel was charged with the acid chloride/toluene solution prepared in Step A (~125 mL). This toluene solution was added dropwise to the aqueous reaction over approximately 10 minutes at ~10° C. Once the addition was complete, the reaction was warmed to room temperature (~22-25° C.) and vigorously stirred for 3 h. The reaction mixture was then transferred to a separatory funnel and the two layers were separated. The lower aqueous phase was then recharged to the reaction flask. Methanol (125 mL)

was then added to the red solution followed by pH adjustment (target pH=1-2) with 3.0 M HCl (~175 mL), keeping the temperature at 15-20° C. Some off-gassing occurred at ~pH=5, followed by precipitation of the product at pH=3. The slurry was allowed to stir at room temperature for 30 minutes at ambient temperature post pH adjustment. The resulting pink solid precipitate was collected by vacuum filtration, (mother liquor losses<2 mg/mL), washed with deionized water (1×50 ml) then dried in a vacuum oven at 40° C. with a nitrogen sweep to a constant weight to provide 11.92 g (0.43.9 mmol, 36%) of the title compound with an HPLC purity of 99 A %. $^1$H NMR (d6-DMSO, 400 MHz) δ 13.04 (s, 1H), 9.14 (d, 1H, J=1.44 Hz), 8.88 (dd, 2H, J=2.48, 6.16 Hz), 8.75 (dd, 1H, J=1.52, 2.4 Hz), 7.25 (m, 4H), 7.18 (m, 1H), 4.75 (dt, 1H, J=5.48, 8.08 Hz), 3.2 (dd, 2H, J=1.79, 5.32 Hz).

Step C. Preparation of N-[(1S)-1[[[(1R)-1-[3aS,4S,6S,7aR)-hexahydro-3a,5,5-trimethyl-4,6-methano-1,3,2-benzodioxaborol-2-yl]-3-methylbutyl]amino] carbonyl]-2-benzyl]2-pyrazine carboxamide A 500 ml three neck round bottomed flask equipped with a stir bar, addition funnel, thermocouple, nitrogen inlet/outlet and cooling bath was charged with 11 g (99.9 mmol) of (S)-3-Phenyl-2-[(pyrazine-2-carbonyl)-amino]-propionic acid (the product of Step B), 15.5.0 g (40.6 mmol) of O-(7-azabenzotriazol-1-yl)-N,N,N'N'-tetramethyluronium hexafluorophosphate (HATU), 12.2 g (40.6 mmol) of (1R)-1-[(3aS,4S,6S,7aR)-hexahydro-3a,5,5-trimethyl-4,6-methano-1,3,2-benzodioxaborol-2-yl]-3-methylbutylamine hydrochloride salt (87:13 mixture of isobutyl diastereomers (R:S)) and 165 mL of N,N-dimethylformamide (DMF). The pale yellow reaction solution was cooled to −35° C. where 12.6 g (17 mL, 97.3 mmol) of N,N-di-isopropyl ethyl amine was added dropwise over six minutes at −34° C. to −35° C. The resulting solution was then stirred overnight at −40 to −11° C. The reaction mixture was quenched onto 600 ml of a 1:1 cold water/ethyl acetate mixture. After transferring into a separatory funnel the layers were separated. The organic phase was then washed successively with 10% aqueous sodium hydrogen phosphate (1×200 mL), 8% aqueous sodium bicarbonate (2×200 mL) and saturated sodium chloride (1×200 mL). The product solution was dried over magnesium sulfate then filtered. The filtrate was evaporated to dryness in vacuo to give 19.57 g (37.7 mmol, 93%) of the title compound as a light brown foam with an HPLC purity of 92 A %. $^1$H NMR (d6-DMSO, 400 MHz) δ 9.15 (d, 1H, J=1.44 Hz), 8.87 (d, 1H, J=2.48 Hz), 8.7 (m, 3H), 7.25 (m, 4H), 7.18 (m, 1H), 4.89 (q, 1H, J=6.88, 15.4 Hz), 4.13 (dd, 1H, J=1.8, 8.56 Hz), 3.15 (d, 2H, J=6.88 Hz), 2.7 (m, b, 1H), 2.22 (m, b, 1H), 2.05 (m, b, 1H), 1.87 (t, 1H, J=5.40 Hz), 1.81 (s, b, 1H), 1.67 (d, b, 1H), 1.52 (m, b, 1H), 1.13-1.33 (m, 9H), 0.83 (dd, 6H, J=2.48, 6.56 Hz), 0.80 (s, 3H).

Step D. Preparation of (2S)-N-[(1R)-1-(1,3,6,2-dioxazaborocan-2-yl)-3-methylbutyl]-3-phenyl-2-(pyrazin-2-ylformamido)propanamide (i.e., Compound 13)

A one liter four neck round bottomed flask was equipped with an overhead stirrer, thermocouple and nitrogen inlet/outlet then charged with 19.0 g (36.6 mmol) of N-[(1S)-1[[[(1R)-1-[(3aS,4S,6S,7aR)-hexahydro-3a,5,5-trimethyl-4,6-methano-1,3,2-benzodioxaborol-2-yl]-3-methylbutyl] amino]carbonyl]-2-benzyl]2-pyrazine carboxamide (produced as in Step C), 9.32 g (91.5 mmol) of isobutylboronic acid, 190 mL of methanol, 34.7 mL (69.4 mmol) of 2M aqueous hydrochloric acid and 285 mL of heptane. The two phase reaction was stirred at room temperature overnight until an IPC showed <2% starting material remaining by area. The reaction mixture was transferred to a separatory funnel and the layers were separated. The lower methanol layer was washed with heptanes (2×250 mL) before being removed to a one-liter round bottomed flask and evaporating to dryness in vacuo. The resulting residue was dissolved in 300 mL of ethyl acetate which was washed with 8% aqueous sodium bicarbonate (2×200 mL) and brine (1×300 mL), before transferring to a clean one liter three neck round bottom flask equipped as above.

To the ethyl acetate solution was added 4.1 g (38.4 mmol) of diethanolamine and the mixture was stirred at room temperature over the weekend. The resulting solids were collected by vacuum filtration, washed with ethyl acetate (1×30 mL) then dried in a vacuum oven at 50° C. overnight to provide the title compound as a white solid (15.8 g, 34.9 mmol, 95.2%), which was shown by HPLC to be a 91:9 mixture of diastereomers (i.e., 82% de).

Step E (Optional). Purification of (2S)-N-[(1R)-1-(1,3,6,2-dioxazaborocan-2-yl)-3-methylbutyl]-3-phenyl-2-(pyrazin-2-ylformamido)propanamide (i.e., Compound 13).

(2S)-N-[(1R)-1-(1,3,6,2-dioxazaborocan-2-yl)-3-methylbutyl]-3-phenyl-2-(pyrazin-2-ylformamido)propanamide produced as in Step D was charged to a 250 ml three round-bottom flask equipped with a stir bar, thermocouple, heating mantle, controller, condenser and nitrogen inlet/outlet. Ethanol (absolute, 128 mL) was then charged to the flask and heated to reflux. Not all the solids dissolved and these were removed by vacuum filtration and later shown to be enriched (2:8) in the undesired isomer. The filtrate was returned to the round bottom flask and cooled to room temperature to crystallize the product which was isolated by vacuum filtration, washed with cold absolute ethanol (1×50 ml), and dried in a vacuum oven at 50° C. overnight to provide 11.6 g (25.6 mmol, 70%) of the title compound as a 94:6 mixture of diastereomers (i.e., 88% de). The chemical purity was >99.9 A %. 1H NMR (d6-DMSO, 400 MHz) δ 9.10 (d, 1H, J=1.4 Hz), 8.88 (d, 1H, J=2.48 Hz), 8.83 (d, 1H, J=8.84 Hz), 8.75 (dd, 1H, J=1.52, 2.32 Hz), 7.3 (m, 5H), 6.55 (s, b, 1H), 4.75 (m, 1H), 3.65 (m, 2H), 3.55 (m, 1H), 3.45 (m, 1H), 2.9-3.2 (m, 4H), 2.8 (m, 1H), 2.7 (m, 2H), 1.56 (m, 1H), 1.33 (dt, 1H, J=4.04, 13.80 Hz), 1.18 (dt, 1H, J=3.48, 9.88 Hz), 0.8 (dd, 6H, J=6.64, 12.56 Hz).

Preparation 5. Preparation of bortezomib

A 100 ml three neck round bottom flask was equipped with a stir bar, thermocouple and nitrogen inlet/outlet then charged with 5.0 g (10.4 mmol) of (2S)-N-[(1R)-1-(1,3,6,2-dioxazaborocan-2-yl)-3-methylbutyl]-3-phenyl-2-(pyrazin-2-ylformamido)propan-amide (i.e., Compound 13), 50 ml of methanol and 10.4 ml of 2N aqueous hydrochloric acid. The reaction was stirred at room temperature overnight before removing the solvent in vacuo at 40° C. The resulting residue was dissolved in 50 ml of ethyl acetate and washed with saturated sodium bicarbonate (1×50 mL) before once again concentrating the organic to dryness in vacuo. The residue was then triturated overnight at room temperature with 50 mL of pentane under nitrogen. The resulting free flowing solids were collected by vacuum filtration, washed with pentane (1×20 ml) then dried in a vacuum oven at 30° C. overnight to provide 3.29 g (8.56 mmol, 82.3%) of the title compound as a white solid. HPLC analysis indicated chemical purity>99.8 A % and a 93.5:6.5 ratio of diastereomers (i.e., 87% de). 1H NMR (d4-MeOH, 400 MHz) δ 9.15 (d, 1H, J=1.36 Hz), 8.77 (d, 1H, J=2.48 Hz), 8.68 (dd, 1H, J=1.52, 2.44 Hz), 7.27 (m, 4H), 7.21 (m, 1H), 5.05 (t, 1H, J=7.68 Hz), 3.2 (m, 2H), 2.66 (t, 1H, J=7.56 Hz), 1.39 (m, 1H), 1.17 (t, 2H, J=7.12 Hz), 0.83 (dd, 6H, J=5.32, 6.40 Hz).

Preparation 6. Preparation of 6-Phenyl-pyridine-2-carboxylic acid{(1S,2R)-1-[(R)-1-(4,8-dimethyl-[1,3,6,2-dioxaborocan-2-yl)-3-methylbutylcarbamoyl}-2-2-hydroxypropyl}amide (i.e., Compound 11)

A 50 mL four neck round bottom flask was equipped with a stir bar, thermocouple, heating mantle with temperature controller, condenser and nitrogen inlet then charged with 2.0 g (3.65 mmol) of N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide (chemical purity=95.7%, chiral purity about 97.5% de (based on the fact that the (1R)-1-[(3aS,4S,6S,7aR)-hexahydro-3a,5,5-trimethyl-4,6-methano-1,3,2-benzodioxaborol-2-yl]-3-methyl-butylamine used to make the N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide had a 97.5% de)), 30 mL of t-butyl methyl ether (MTBE) and 0.61 g (94.56 mmol, 1.25 eq) of diisopropanolamine The resultant yellow solution was stirred at 20-25° C. for 16 hours at which point only a small amount of solid had formed. An additional 1.2 g (9 mmol, 2.5 eq) of diisopropanolamine was charged and the mixture was heated at 40° C. for 16 hours before cooling to room temperature. The white solid was collected by vacuum filtration, washed with 15 mL of MTBE then dried under vacuum overnight at 33° C. to yield 1.31 g (2.55 mmol, 70%) of the desired product based on 1H NMR. The chemical purity was 96.8 A % and no diastereomer was detected by HPLC (>99.8% de).

Example 1

Preparation of the Lyophilized Cake of Formulation 1

Table 1 depicts representative quantities of the ingredients used in this Example. A solution of mannitol and hydroxypropyl β cyclodextrin (KLEPTOSE® HP) in Sterile Water for Injection was prepared. Polysorbate 20, tert-butanol, and Compound 1 were stirred at ambient temperature until complete dissolution of the Compound 1 occurred (visual inspection). When a clear and colorless solution, without any visible particulate, was obtained, the mannitol/cyclodextrin solution was added. The resulting solution was stirred until homogeneous and then filtered using a disposable sterile device with a 0.22 µm, PVDF filter (STERICUP®, Millipore, Billerica, Mass.). The filtered solution was filled into 10 mL clear glass type I vials for lyophilization. The solution was lyophilized according to the procedure set forth in Example 7 to provide a lyophilized cake.

Example 2

Preparation of the Lyophilized Cake of Formulation 2

Table 1 depicts representative quantities of the ingredients used in this Example. A solution of hydroxypropyl β cyclodextrin (KLEPTOSE® HP) in Sterile Water for Injection was prepared. In a separate, closed container, tert-butanol and Compound 1 were stirred at ambient temperature until complete dissolution of the Compound 1 occurred (visual inspection). When a clear and colorless solution, without any visible particulate, was obtained, the cyclodextrin solution was added. The resulting solution was stirred until homogeneous and then filtered using a disposable sterile device with a 0.22 µm, PVDF filter (STERICUP®, Millipore, Billerica, Mass.). The filtered solution was filled to 4 mL into 10 mL clear glass type I vials for lyophilization. The solution was lyophilized according to the procedure set forth in Example 7 to provide a lyophilized cake.

Example 3

Preparation of the Lyophilized Cake of Formulation 3

Table 1 depicts representative quantities of the ingredients used in this Example. A solution of mannitol in Sterile Water for Injection was prepared. In a separate, closed container, tert-butanol and Compound 1 were stirred at ambient temperature until complete dissolution of the Compound 1 occurred (visual inspection). When a clear and colorless solution, without any visible particulate, was obtained, the mannitol solution was added. The resulting solution was stirred until homogeneous and then filtered using a disposable sterile device with a 0.22 µm, PVDF filter (STERICUP®, Millipore, Billerica, Mass.). The filtered solution was filled to 4 mL into 10 mL clear glass type I vials for lyophilization. The solution was lyophilized according to the procedure set forth in Example 7 to provide a lyophilized cake.

Example 4

Preparation of the Lyophilized Cake of Formulation 4

Table 1 depicts representative quantities of the ingredients used in this Example. A solution of mannitol and hydroxypropyl β cyclodextrin (KLEPTOSE® HP) in Sterile Water for Injection was prepared. In a separate, closed container, tert-butanol and Compound 1 were stirred at ambient temperature until complete dissolution of the Compound 1 occurred (visual inspection). When a clear and colorless solution, without any visible particulate, was obtained, the mannitol/cyclodextrin solution was added. The resulting solution was stirred until homogeneous and then filtered using a disposable sterile device with a 0.22 µm, PVDF filter (STERICUP®, Millipore, Billerica, Mass.). The filtered solution was filled into 10 mL clear glass type I vials for lyophilization. The solution was lyophilized according to the procedure set forth in Example 7 to provide a lyophilized cake.

Example 5

Preparation of the Lyophilized Cake of Formulation 5

Table 1 depicts representative quantities of the ingredients used in this Example. A solution of hydroxypropyl β cyclodextrin (KLEPTOSE® HP) in Sterile Water for Injection was prepared. In a separate, closed container, Polysorbate 20, tert-butanol, and Compound 1 were stirred at ambient temperature until complete dissolution of the Compound 1 occurred (visual inspection). When a clear and colorless solution, without any visible particulate, was obtained, the cyclodextrin solution was added. The resulting solution was stirred until homogeneous and then filtered using a disposable sterile device with a 0.22 μm, PVDF filter (STERICUP®, Millipore, Billerica, Mass.). The filtered solution was filled to 4 mL into 10 mL clear glass type I vials for lyophilization. The solution was lyophilized according to the procedure set forth in Example 7 to provide a lyophilized cake.

Example 6

Preparation of the Lyophilized Cake of Formulation 6

Table 1 depicts representative quantities of the ingredients used in this Example. A solution of mannitol and hydroxypropyl β cyclodextrin (KLEPTOSE® HP) in Sterile Water for Injection was prepared. Polysorbate 20, Compound 1, and about $1/10^{th}$ of the mannitol/cyclodextrin solution were stirred at about 35° C. until complete dissolution of the Compound 1 occurred (visual inspection). When a clear and colorless solution, without any visible particulate, was obtained, the remaining mannitol/cyclodextrin solution was added. The resulting solution was stirred until homogeneous and then filtered using a disposable sterile device with a 0.22 μm, PVDF filter (STERICUP®, Millipore, Billerica, Mass.). The filtered solution was filled to 4 mL into 10 mL clear glass type I vials for lyophilization. The solution was lyophilized according to the procedure set forth in Example 7 to provide a lyophilized cake.

lyophilization procedure, the shelf temperature is ramped to 30° C. (2° C./min) and held for 18 h. At the end of the freeze-drying process, the vials were closed under vacuum. After unloading from the freeze-dryer, aluminum seals were crimped over the rubber stoppers.

Example 8

Lyophilization Procedure—Method B

For those formulations containing a surfactant, for example polysorbate, the following lyophilization procedure can be used. Freeze the solution to about −40° C. and hold for about 5 h. Apply vacuum at about 80 μm and ramp to about 25° C. for primary drying, holding for 18 h. Secondary drying is performed at about 25° C., holding for 10 h.

Example 9

Lyophilization Procedure—Method C

For those formulations containing tert-butanol, the following lyophilization procedure can be used. Freeze the solution to about −40° C. and hold for about 4 h. Ramp to about −11° C. and hold for about 4 h and then ramp to about −40° C. and hold for about 4 h. Apply vacuum at about 80 μm and ramp to

TABLE 1

| Ingredient (mg/g) | Formulation 1 | Formulation 2 | Formulation 3 | Formulation 4 | Formulation 5 | Formulation 6 |
|---|---|---|---|---|---|---|
| Compound 1 | 1 | 1 | 1 | 1 | 1 | 1 |
| Polysorbate 20 | 20 | — | — | — | 20 | 20 |
| Kleptose ® HP | 49 | 50 | — | 49 | 49 | 49 |
| Mannitol | 39.2 | — | 50 | 39.2 | — | 39.2 |
| Sterile water for injection | 618 | 637 | 637 | 598.8 | 618 | 890.8 |
| Tert-butanol | 312* | 312 | 312* | 312* | 312* | — |
| (Total dry mass) (mg) | (109.2) | (51) | (51) | (89.2) | (70) | (109.2) |
| Total (mg) | 1000 | 1000 | 1000 | 1000 | 1000 | 1000 |

*corresponding to 40% tert-butanol v/v in the formulation (density 0.78)

Example 7

Lyophilization Procedure—Method A

This Example sets forth one preferred lyophilization cycle suitable for use with the formulations described herein. Using a LABCONCO TRIAD® freeze dryer, the solution is loaded at a shelf temperature of about 0° C. and then brought to a congealing temperature of about −40° C. In the first segment of the lyophilization procedure, the shelf temperature is ramped to −30° C. (5 C/min) and the pressure brought to 100 μbar and held for 0.2 h. In the second segment of the lyophilization procedure, the shelf temperature is ramped to 20° C. (2° C./min) and held for 4 h. In the third segment of the about 25° C. for primary drying, holding for about 18 h. Ramp to about 30° C. for secondary drying, holding for about 20 h.

Example 10

Evaluation of Formulations 2, 3, and 4 Prior to Freeze-Drying

Analysis of the pre-lyophilization solutions for Formulations 2, 3, and 4 were performed at $t_0$ and after 48 hours storage at 25° C. and 60% relative humidity. The results are shown in Table 2 below. Each of Formulations 2, 3, and 4 were clear colorless solutions. The change in purity over the storage period is within experimental error and is not considered significant.

TABLE 2

| Time | Attribute | Formulation 2 | Formulation 3 | Formulation 4 |
|---|---|---|---|---|
| T0 | Appearance | Clear colorless solutions | | |
| | Assay (mg/mL) | 1.02 | 1.02 | 0.97 |
| | Compound 1 purity (%) | 97.1 | 97.8 | 96.4 |
| | pH | 7.7 | 6.0 | 5.8 |

TABLE 2-continued

| Time | Attribute | Formulation 2 | Formulation 3 | Formulation 4 |
|---|---|---|---|---|
| After 48 h at 25° C./60% RH | Appearance | Clear colorless solutions | | |
| | Assay (mg/mL) | 0.94 | 0.96 | 0.97 |
| | Compound 1 purity (%) | 96.6 | 97.8 | 96.2 |
| | pH | ND | ND | 5.8 |

Compound 1 purity % calculated using the following equation:

(Area of Compound 1÷total area of injected sample)× 100%=Compound 1 purity (%)

Example 11

Evaluation of Lyophilized Formulation 2

Formulation 2 was evaluated for its reconstitution profile and stability after storage of the lyophilized cake for 15 days, 1 month, 2 months, and 3 months at 40° C. and 75% relative humidity. Samples were reconstituted with 3.8 mL of deionized water. Formulation 2, after lyophilization, was a white powder that was very difficult to dissolve. Even with vigorous manual shaking, fine particles were observed to remain in solution. The solution was filtered through a 0.45 mm filter and analyzed by HPLC. The results are shown in Table 3A.

TABLE 3A

| | Evaluation of Formulation 2 | | | | |
|---|---|---|---|---|---|
| Test | Initial time | 15 days | 1 month | 2 months | 3 months* |
| Appearance | White powder, hard to dissolve (need vigorous manual shaking). Frothy and cloudy solution with fine particles in suspension | | | | |
| pH (n = 3) | 7.5 | 7.2 | 7.5 | 6.8 | 6.8 |
| Assay of Compound 1 by HPLC (n = 3) (mg/mL) | 0.96 ± 0.7% RSD | | | NA | |
| Compound 1 purity by HPLC (%) | 97.2 | 96.5 | 96.5 | 96.6 | 96.0 |

Example 12

Evaluation of Lyophilized Formulation 3

Formulation 3 was evaluated for its reconstitution profile and stability after storage of the lyophilized cake for 15 days, 1 month, 2 months, and 3 months at 40° C. and 75% relative humidity. Samples were reconstituted with 3.8 mL of deionized water. Formulation 3, after lyophilization, was a white powder that was very difficult to dissolve. Even with vigorous manual shaking, fine particles were observed to remain in solution. The solution was filtered through a 0.45 mm filter and analyzed by HPLC. The results are shown in Table 3B.

TABLE 3B

| | Evaluation of Formulation 3 | | | | |
|---|---|---|---|---|---|
| Test | Initial time | 15 days | 1 months | 2 months | 3 months* |
| Appearance | White powder, hard to dissolve (need vigorous hand shaking). Frothy and cloudy solution with fine particles in suspension | | | | |
| pH | 5.7 | 6.0 | 5.9 | 5.4 | 5.4 |
| Assay of Compound 1 by HPLC (n = 3) (mg/mL) | 0.81 ± 1.1% RSD | | | NA | |
| Compound 1 purity by HPLC (%) | 98.0 | 97.0 | 97.0 | 96.5 | 96.2 |

Example 13

Evaluation of Formulation 4

Formulation 4 was evaluated for its reconstitution profile and stability after storage of the lyophilized cake for 15 days, 1 month, 2 months, and 3 months at 40° C. and 75% relative humidity. Samples were reconstituted with 3.64 mL of deionized water. In contrast to Formulation 2, which contains only cyclodextrin, and Formulation 3, which only contains mannitol, Formulation 4, which includes both cyclodextrin and mannitol, was a white powder after lyophilization and was easily and rapidly dissolved in less than 30 seconds to form a clear and colorless, particulate free solution. In addition, although the drug purity in the lyophilized cakes of Formulations 2 and 3 decreased by greater than 1% after storage for 3 months under accelerated conditions, the drug purity in the lyophilized cake of Formulation 4 was stable, exhibiting no decrease in drug purity. The results are shown in Table 3C.

TABLE 3C

| Evaluation of Formulation 4 | | | | | |
|---|---|---|---|---|---|
| Test | Initial time | 15 days | 1 month | 2 months | 3 months |
| Appearance | White powder, easy and rapid dissolved (< 30s) Clear and colorless solution | | | | |
| pH | 5.8 | 5.5 | 5.4 | 5.5 | 5.6 |
| Assay of Compound 1 by HPLC (n = 3) (mg/mL) | 0.94 ± 0.3% RSD | | | NA | |
| Compound 1 purity by HPLC (%) | 96.1 | 96.4 | 96.4 | 96.4 | 96.5 |
| RRT 1.61 | 0.06 | 0.05 | 0.05 | | |

Example 14

Evaluation of Formulations 1, 5, and 6 Upon Reconstitution

Formulations 1, 5, and 6 were evaluated for their reconstitution profile. Samples of each formulation were reconstituted with Sterile Water for Injection. Dissolution occurred in 90 seconds or less for each of Formulations 1 and 6 to produce clear, colorless, particulate-free solutions. Upon reconstitution, no solids were observed to have precipitated. Formulation 5 was dissolved in about 2 minutes to produce a clear, colorless solution, free of particulate.

Example 15

Determination of Residual Tert-Butanol After Lyophilization of Formulation 4

Tert-butanol levels were measured using a gas chromatography headspace method. It was determined that after lyophilization of Formulation 4, between about 2.73% w/w and about 2.85% w/w was detected in the lyophilized cake.

Example 16

Six Month Storage Stability Data for Formulation 1

A six month stability study was carried out on freeze-dried Formulation 1. Three storage conditions were evaluated: about 5° C. at ambient relative humidity, about 25° C. at about 60% relative humidity, and about 40° C. at about 75% relative humidity. Table 4 shows the results of this stability study. After 6 months of storage, the drug purity in the lyophilized cake of Formulation 1 was unchanged under refrigerated conditions, decreased by 0.1% under room temperature conditions, and decreased by 1.0% under accelerated conditions.

TABLE 4

| Six Month Storage Stability Data for Formulation 1 | | | | |
|---|---|---|---|---|
| Test | Initial time | 5° C./ ambient RH | 25° C./ 60% RH | 40° C./ 75% RH |
| Appearance | White | White | White | White |
| pH | 5.7 | 5.3 | 5.1 | 5.2 |
| Residual humidity* (% H$_2$O) | 1 | 1.8 | 1.3 | 1.4 |
| Compound 1 purity by HPLC (Area %) | 98.1 | 98.1 | 98.0 | 97.1 |

*this test was performed on placebo due to toxicity of Compound 1.

Example 17

Six Month Storage Stability Data for Formulation 4

A six month stability study was carried out on freeze-dried Formulation 4. Three storage conditions were evaluated: about 5° C. at ambient relative humidity, about 25° C. at about 60% relative humidity, and about 40° C. at about 75% relative humidity. Table 5 shows the results of this stability study. After 6 months of storage, the drug purity in the lyophilized cake of Formulation 4 was unchanged under refrigerated conditions and under room temperature conditions, and decreased by 0.5% under accelerated conditions.

TABLE 5

| Six Month Storage Stability Data for Formulation 4 | | | | |
|---|---|---|---|---|
| Test | Initial time | 5° C./ ambient RH | 25° C./ 60% RH | 40° C./ 75% RH |
| Appearance | White | White | White | White |
| pH | 5.5 | 5.6 | 5.3 | 5.2 |
| Residual humidity* (% H$_2$O) | 1.8 | 2.0 | 1.2 | 1.7 |
| Compound 1 purity by HPLC (Area %) | 98.1 | 98.2 | 98.1 | 97.6 |

*this test was performed on placebo due to toxicity of Compound 1.

Example 18

Six Month Storage Stability Data for Formulation 5

A six month stability study was carried out on freeze-dried Formulation 5. Three storage conditions were evaluated: about 5° C. at ambient relative humidity, about 25° C. at about 60% relative humidity, and about 40° C. at about 75% relative humidity. Table 6 shows the results of this stability study. After 6 months of storage, the drug purity in the lyophilized cake of Formulation 5 decreased by 0.2% under refrigerated conditions, decreased by 1% under room temperature conditions, and decreased by 8.7% under accelerated conditions.

TABLE 6

Six Month Storage Stability Data for Formulation 5

| Test | Initial time | 5° C./ ambient RH | 25° C./ 60% RH | 40° C./ 75% RH |
|---|---|---|---|---|
| Appearance | White | White | White | White |
| pH | 6.3 | 6.3 | 6.0 | 5.7 |
| Residual humidity* (% H$_2$O) | ND | 1.7 | 1.9 | 2.3 |
| Compound 1 purity by HPLC (Area %) | 98.0 | 97.8 | 97.0 | 89.3 (n = 2) |

*this test was performed on placebo due to toxicity of Compound 1.

Example 19

Six Month Storage Stability Data for Formulation 6

A six month stability study was carried out on freeze-dried Formulation 6. Three storage conditions were evaluated: about 5° C. at ambient relative humidity, about 25° C. at about 60% relative humidity, and about 40° C. at about 75% relative humidity. Table 7 shows the results of this stability study. After 6 months of storage, the drug purity in the lyophilized cake of Formulation 6 decreased by 0.2% under refrigerated conditions, decreased by 0.9% under room temperature conditions, and decreased by 8.1% under accelerated conditions.

TABLE 7

Six Month Storage Stability Data for Formulation 6

| Test | Initial time | 5° C./ ambient RH | 25° C./ 60% RH | 40° C./ 75% RH |
|---|---|---|---|---|
| Appearance | White | White | White | White |
| pH | 5.5 | 5.5 | 5.5 | 5.3 |
| Residual humidity* (% H$_2$O) | ND | 1.0 | 1.2 | 1.4 |
| Compound 1 purity by HPLC (Area %) n = 2 | 97.7 | 97.5 | 96.8 | 89.6 (n = 2) |

*this test was performed on placebo due to toxicity of Compound 1.

As demonstrated by the preceding Examples, formulations including cyclodextrin and a surfactant (i.e., Formulations 1, 5, and 6) or cyclodextrin and a bulking agent (i.e., Formulation 4) were reconstituted within two minutes to provide clear, colorless, particulate-free solutions. Formulations with either cyclodextrin only (i.e., Formulation 2) or bulking agent only (i.e., Formulation 3) did not produce particulate-free solutions upon reconstitution, indicating that these formulations would be unsuitable for intravenous use.

Additionally, the preceding Examples demonstrate that formulations prepared using an organic solvent and a bulking agent can be more stable than those prepared without one of these ingredients (compare Formulation 1 with Formulations 5 and 6). In addition, including a surfactant does not appear to increase stability (compare Formulations 1 and 4).

Notably, Formulation 4 demonstrated excellent stability over the course of each study period tested and provided a clear, colorless, particulate-free solution within 30 seconds upon reconstitution. These qualities make Formulation 4 well suited for injection.

Example 20

Large Scale Processes for Preparation of the Lyophilized Cake of Formulation 4

Batch A

A solution of mannitol and hydroxypropyl β cyclodextrin (KLEPTOSE® HP) in Sterile Water for Injection was prepared. In a separate, closed container, tert-butanol and Compound 1 were stirred at ambient temperature until complete dissolution of the Compound 1 occurred (visual inspection). About 1.5 h was needed for the dissolution of a total batch size of about 160 g. When a clear and colorless solution, without any visible particulate, was obtained, the mannitol/cyclodextrin solution was added. The resulting solution was stirred until homogeneous and then filtered using a disposable sterile device with a 0.22 μm, PVDF filter (STERICUP®, Millipore, Billerica, Mass.). The filtered pre-lyophilization solution was filled into to 4 mL into 10 mL clear glass type I vials for lyophilization. The pre-lyophilization solution was lyophilized according to the procedure set forth in Example 7.

Batch B

General. All steps are performed in a suitable clean room with aseptic procedure. The drug product is filled in an ISO 5 processing suite. Bulk solutions are formulated in dedicated vessels with dedicated and disposable utensils. Prior to the sterile filtration of the drug product all disposable items and containers used were either pre-sterilized or rinsed with sterile water for injection.

Step 1. A solution of Compound 1 (4.2 g) in tert-butyl alcohol (1.31 kg) is prepared by adding the Compound 1 to the tert-butyl alcohol and mixing in a suitable container until a clear solution is formed.

Step 2. A solution of mannitol (164.6 g) and hydroxypropyl-β-cyclodextrin (HPβCD; 205.8 g) is prepared by adding mannitol and HPβCD to sterile water for injection (2.515 kg) and mixing until a clear solution is formed.

Step 3. The solution prepared in Step 2 (mannitol/HPβCD solution) is slowly added to the solution prepared in Step 1 (tert-butyl alcohol/Compound 1) and mixed in a suitable container until a clear solution is formed.

Step 4. The finished solution from Step 3 (pre-lyophilization solution) is sterile filtered into a sterile receiving vessel and protected from light.

Step 5. The sterile filtered solution is dispensed into 1,050 washed and deprogenated 20 mL Type I glass tubing vials (4 g/vial).

Step 6. Sterilized stoppers are partially inserted and the filled vials are placed onto trays into a sterile lyophilizer chamber. The vials are then lyophilized. At the completion of the lyophilization process, the vials are stoppered in the lyophilizer under vacuum with a nitrogen atmosphere and sealed with aluminum crimp seals.

Tables 8-11 provide storage stability data for the lyophilized cakes of Batch B under refrigerated, room temperature, enhanced room temperature, and accelerated conditions. Total impurity content by HPLC (area %) is provided. Also provided is purity content by HPLC for individual impurities present at >0.1% under any of the conditions (i.e., Impurities A, B and C—see structures below).

TABLE 8

Stability Data for Batch B Stored at 5° C.

| Impurity | Initial time | 3 month | 6 months | 9 months | 12 months |
|---|---|---|---|---|---|
| A (Area %) | 0.6 | 0.6 | 0.6 | 0.6 | 0.5 |
| B (Area %) | <LOQ | 0.1 | 0.1 | 0.1 | 0.1 |
| C (Area %) | <LOQ | <LOQ | <LOQ | ND | ND |
| Total (Area %) | 0.6 | 0.7 | 0.6 | 0.6 | 0.6 |

LOQ—Limit of Quantitation
ND—Not Detected

The impurity content of the lyophilized cake remained constant for 12 months, indicating that after storage for 3, 6, 9 or 12 months under refrigerated conditions the lyophilized cake contained no degradation impurities. Even though the quantity of Impurity B increased during storage, the increase was not due to degradation of Compound 1, but rather to degradation of Impurity A.

TABLE 9

Stability Data for Batch B Stored at 25° C./60% RH

| Impurity | Initial time | 1 month | 3 months | 6 months | 9 months | 12 months |
|---|---|---|---|---|---|---|
| A (Area %) | 0.6 | 0.5 | 0.5 | 0.5 | 0.4 | 0.3 |
| B (Area %) | <LOQ | 0.1 | 0.1 | 0.2 | 0.2 | 0.2 |
| C (Area %) | <LOQ | <LOQ | <LOQ | <LOQ | <LOQ | <LOQ |
| Total (Area %) | 0.6 | 0.6 | 0.6 | 0.6 | 0.7 | 0.6 |

The impurity content of the lyophilized cake remained constant for 12 months, indicating that after storage for 3, 6, 9 or 12 months under room temperature conditions the lyophilized cake contained no degradation impurities. Even though the quantity of Impurity B increased during storage, the increase was due to degradation of Impurity A, not degradation of Compound 1.

TABLE 10

Stability Data for Batch B Stored at 30° C./65% RH

| Impurity | Initial time | 6 months | 12 months |
|---|---|---|---|
| A (Area %) | 0.6 | 0.4 | 0.2 |
| B (Area %) | <LOQ | 0.3 | 0.3 |
| C (Area %) | <LOQ | 0.1 | 0.1 |
| Total (Area %) | 0.6 | 0.7 | 0.7 |

The impurity content of the lyophilized cake remained constant for 12 months, indicating that after storage for 6 or 12 months under enhanced room temperature conditions the lyophilized cake contained no degradation impurities. Even though the quantities of Impurities B and C increased during storage, the increases were due to degradation of Impurities A and B, respectively, not degradation of Compound 1.

TABLE 11

Stability Data for Batch B Stored at 40° C./75% RH

| Impurity | Initial time | 1 month | 3 months | 6 months | 12 months |
|---|---|---|---|---|---|
| A (Area %) | 0.6 | 0.4 | 0.3 | 0.2 | 0.1 |
| B (Area %) | <LOQ | 0.2 | 0.4 | 0.5 | 0.6 |
| C (Area %) | <LOQ | <LOQ | 0.1 | 0.1 | 0.2 |
| Total (Area %) | 0.6 | 0.6 | 0.8 | 0.9 | 1.0 |

The impurity content of the lyophilized cake increased by about 0.2% after 3 months, 0.3% after 6 months and 0.4% after 12 months, indicating that after storage for 12 months under accelerated conditions the lyophilized cake contained less than 0.5% w/w of degradation impurities. Even though the quantities of Impurities B and C increased during storage, the increases were due to degradation of Impurities A and B, respectively, not degradation of Compound 1.

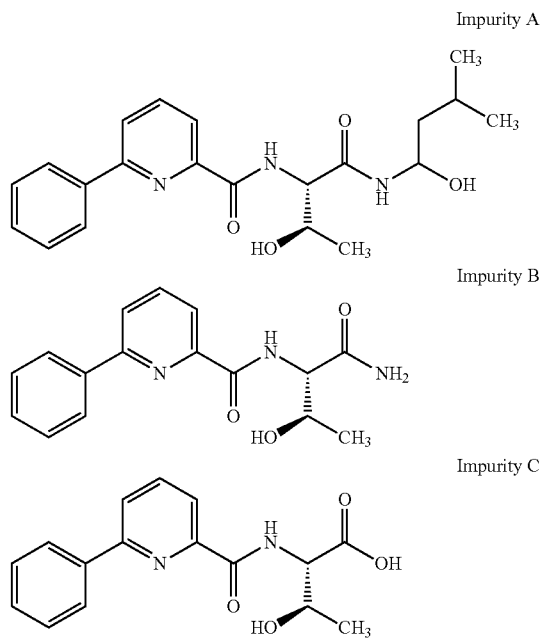

Example 21

Preparation of Lyophilized Cakes of Formulations 7 and 8

Mannitol (39.2 mg) and Kleptose® HP (hydroxypropyl-β-cyclodextrin; 49 mg) are dissolved in sterile water for injection (599 mg) at room temperature. Compound 10 (1.167 mg) is dispersed in tert-butanol (312 mg) by magnetic stirring protected from light at room temperature during 10 minutes. A few mL of the Mannitol/Kleptose® solution is poured into the Compound 10 dispersion in order to solubilize the Compound 10. After forming a solution, the remaining Mannitol/Kleptose® solution is added. The solution is stirred for a few minutes while protected from light. In Formulation 7, the pH is adjusted with phosphoric acid (2M) down to pH 4.0±0.2. In Formulation 8, the pH is about 8 and is not adjusted. The pre-lyophilization solution is filtered through a sterile disposable PVDF filter of 0.22 μm (Stericup Millipore®) to form a clear solution. 4 mL of the filtered pre-lyophilization solution is transferred into a 10 mL bottle and then freeze-dried. Because Compound 10 is readily hydrolyzed in aqueous solution, the obtained lyophilized cake contains >3.99 mg Compound 1 and <0.01 mg Compound 10.

Example 22

Evaluation of Formulations 7 and 8 Prior to Freeze-Drying

Analysis of the pre-lyophilization solutions for Formulations 7 and 8 were performed at $T_0$ and after 48 hours storage at 25° C. Compound 1 was analyzed because Compound 10 is known to convert to Compound 1 in aqueous solution. The results are shown in Table 12 below. The formulation with pH adjustment by addition of phosphoric acid (Formulation 7) is stable without any purity change after 48 h stored at 25° C. However, the formulation without pH adjustment (Formulation 8), which has a pH of ~8, is less stable with a loss of ~2% in purity after 48 h storage at 25° C.

TABLE 12

| Time | Condition | Formulation 7 | Formulation 8 |
|---|---|---|---|
| Solution at Initial time | pH of the solution | 4.1 | 8.1 |
| | Assay of Compound 1 (mg/mL) | 0.97 mg/mL | 0.92 mg/mL |
| | Purity (Compound 1 Area %) | 99.8% | 99.3% |
| Solution after 48 stored at 25° C. | Assay of Compound 1 (mg/mL) | 0.98 mg/mL | 1.0 mg/mL |
| | Purity (Compound 1 Area %) | 99.8% | 97.7% |

Example 23

Evaluation of Lyophilized Cakes of Formulations 7 and 8

The lyophilized cakes of formulations 7 and 8 were evaluated for reconstitution profile and stability after storage for 1 to 6 months at 2-8° C., 25° C./60% RH, and 40° C./75% RH. Samples were reconstituted with water to a target concentration of 1 mg/mL in Compound 1. The reconstituted solution was filtered and analyzed by HPLC. The results are shown in Tables 13-18.

As shown in the Tables, Formulation 7, whose lyophilized cake was pH adjusted to pH 4.1, showed a good stability for at least 6 months. No decrease of Compound 1 purity was observed at 2-8° C. At 25° C./60% RH, the drug purity was unchanged for 3 months and decreased by only 0.1% after 6 months. At 40° C./75% RH, drug purity decreased by only 0.4% after 3 months and 0.6% after 6 months.

Formulation 8, whose lyophilized cake had a pH of 8.1, showed after only one month some trend of degradation. After storage for one month, a decrease in drug purity of 0.3% and 0.9% was observed at 25° C./60% RH and 40° C./75% RH, respectively. After 6 months, the decrease in drug purity was 0.7% and 5.2% respectively.

TABLE 13

Stability Data for Formulation 7 Stored at 2-8° C.

| Test | Initial time | 1 month | 2 months | 3 months | 6 months |
|---|---|---|---|---|---|
| Reconstitution time | 50 sec | NA | <35 sec | <30 sec | NA |
| Appearance | Clear colorless solutions | Similar to Initial time | Similar to Initial time | Similar to Initial time | Similar to Initial time |
| pH | 5.0 | NA | 5.0 | 5.0 | 4.8 |
| Compound 1 by HPLC (area %) (mean of 3 samples) | 99.7 | 99.7 | 99.8 | 99.8 | 99.8 |

TABLE 14

Stability Data for Formulation 7 Stored at 25° C./60% RH

| Test | Initial time | 1 month | 2 months | 3 months | 6 months |
|---|---|---|---|---|---|
| Reconstitution time | 50 sec | NA | <35 sec | <30 sec | NA |
| Appearance | Clear colorless solutions | Similar to Initial time | Similar to Initial time | Similar to Initial time | Similar to Initial time |
| pH | 5.0 | NA | 4.7 | 4.9 | 4.5 |
| Compound 1 by HPLC (area %) (mean of 3 samples) | 99.7 | 99.8 | 99.8 | 99.7 | 99.6 |

TABLE 15

Stability Data for Formulation 7 Stored at 40° C./75% RH

| Test | Initial time | 1 month | 2 months | 3 months | 6 months |
|---|---|---|---|---|---|
| Reconstitution time | 50 sec | NA | <35 sec | <30 sec | NA |
| Appearance | Clear colorless solutions | Similar to Initial time | Similar to Initial time | Similar to Initial time | Similar to Initial time |
| pH | 5.0 | NA | 4.6 | 4.8 | 4.6 |
| Compound 1 by HPLC (area %) (mean of 3 samples) | 99.7 | 99.6 | 99.5 | 99.3 | 99.1 |

TABLE 16

Stability Data for Formulation 8 Stored at 2-8° C.

| Test | Initial time | 1 month | 2 months | 3 months | 6 months |
|---|---|---|---|---|---|
| Reconstitution time | 35 sec | <30 sec | 30 sec. | ~35 sec. | NA |
| Appearance | Clear colorless solutions | Similar to Initial time | Similar to Initial time | Similar to Initial time | Similar to Initial time |
| pH | 8.1 | 7.8 | 7.7 | 7.9 | 7.8 |
| Compound 1 by HPLC (area %) (mean of 3 samples) | 99.6 | 99.7 | 99.7 | 99.5 | 99.5 |

TABLE 17

Stability Data for Formulation 8 Stored at 25° C./60% RH

| Test | Initial time | 1 month | 2 months | 3 months | 6 months |
|---|---|---|---|---|---|
| Reconstitution time | 35 sec | <30 sec | 30 sec. | ~35 sec. | NA |
| Appearance | Clear colorless solutions | Similar to Initial time | Similar to Initial time | Similar to Initial time | Similar to Initial time |
| pH | 8.1 | 7.7 | 7.7 | 7.8 | 7.8 |
| Compound 1 by HPLC (area %) (mean of 3 samples) | 99.6 | 99.3 | 99.4 | 99.1 | 98.9 |

TABLE 18

Stability Data for Formulation 8 Stored at 40° C./75% RH

| Test | Initial time | 1 month | 2 months | 3 months | 6 months |
|---|---|---|---|---|---|
| Reconstitution time | 35 sec | <30 sec | 30 sec. | ~35 sec. | NA |
| Appearance | Clear colorless solutions | Similar to Initial time | Similar to Initial time | Similar to Initial time | Similar to Initial time |
| pH | 8.1 | 7.7 | 7.7 | 7.7 | 7.6 |
| Compound 1 by HPLC (area %) (mean of 3 samples) | 99.6 | 98.7 | 97.8 | 96.8 | 94.4 |

Example 24

Preparation and evaluation of Pre-Lyophilization Solutions of Formulations 9-13

Pre-lyophilization solutions of Formulations 9-13 were prepared in a manner similar to Formulations 7 and 8 with pH adjustment as shown in Table 19. The pre-lyophilization solutions had an initial drug purity (Compound 1 by HPLC) of 99.7%. The pre-lyophilization solutions were stored for one week under stressed conditions at 50° C., and drug purity was again analyzed by HPLC. The results are shown in Table 19.

TABLE 19 pH, Storage Stability of Pre-Lyophilization Solutions of Formulations 9-13

| Formulation | Acid Used to Adjust pH | pH | Drug purity after storing one week at 50° C. (%) |
|---|---|---|---|
| 9 | — | 8.1 | 56.6 |
| 10 | H₃PO₄ | 3.8 | 98.9 |
| 11 | H₃PO₄ | 6.0 | 95.5 |
| 12 | Acetic acid | 4.6 | 98.5 |
| 13 | Acetic acid | 6.0 | 95.0 |

The results showed the benefit of maintaining the pH lower than 8, with greater solution stability at lower pH and the best solution stability obtained at the lowest pH tested.

Representative Embodiments

Representative embodiments of the present invention include the following:

Embodiment #1

A lyophilized cake comprising (a) a drug, wherein the drug is a compound of Formula I, Formula II, or a pharmaceutically acceptable salt or ester thereof:

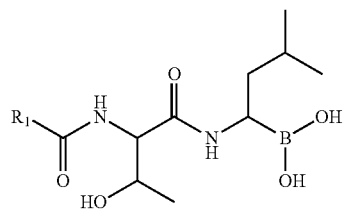

I

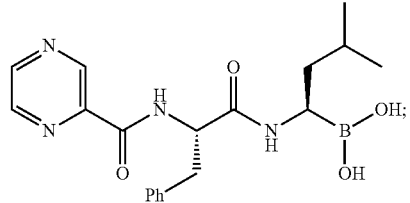

II wherein $R_1$ is an optionally substituted 5-, 6-, or 10-membered heteroaryl having at least one N or $R_1$ is an optionally substituted 6- or 10-membered aryl;
(b) a cyclodextrin; and
(c) at least one member selected from the group consisting of bulking agents and surfactants.

Embodiment #1A

A method for manufacturing a lyophilized cake, comprising the step of lyophilizing a mixture comprising
(a) a drug chosen from a compound of Formula I, Formula II, or a pharmaceutically acceptable salt or ester thereof:

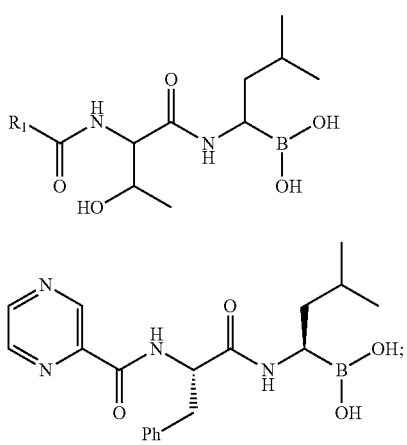

wherein $R_1$ is an optionally substituted 5-, 6-, or 10-membered heteroaryl having at least one N or $R_1$ is an optionally substituted 6- or 10-membered aryl;
(b) a cyclodextrin; and
(c) at least one member selected from the group consisting of bulking agents and surfactants.

Embodiment #1B

A lyophilized cake comprising (a) a drug, wherein the drug is a compound of Formula I, Formula II, or a pharmaceutically acceptable salt or ester thereof:

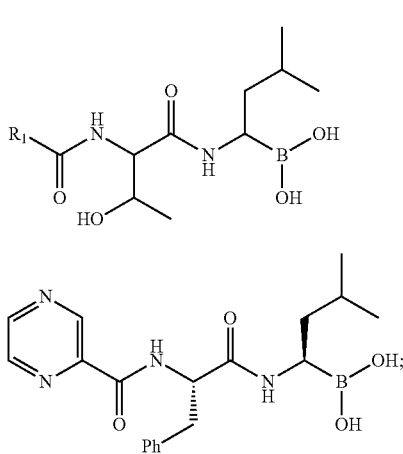

wherein $R_1$ is an optionally substituted 5-, 6-, or 10-membered heteroaryl having at least one N or $R_1$ is an optionally substituted 6- or 10-membered aryl;
(b) a cyclodextrin; and
(c) a bulking agent.

Embodiment #2

The lyophilized cake of Embodiment 1 or the method of Embodiment 1A, wherein the cyclodextrin is present in an amount effective to stabilize the drug after lyophilization.

Embodiment #3

The lyophilized cake of Embodiment 1 or the method of Embodiment 1A, wherein the drug is a compound of formula

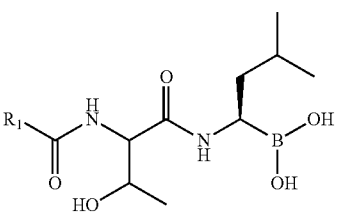

or a pharmaceutically acceptable salt or ester thereof.

Embodiment #3A

The lyophilized cake of Embodiment 1 or the method of Embodiment 1A, wherein the drug is a compound of formula

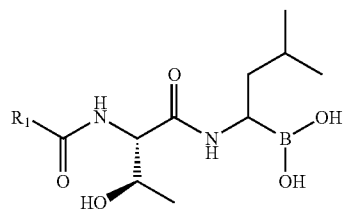

or a pharmaceutically acceptable salt or ester thereof.

Embodiment #3B

The lyophilized cake of Embodiment 1 or the method of Embodiment 1A, wherein the drug is a compound of formula

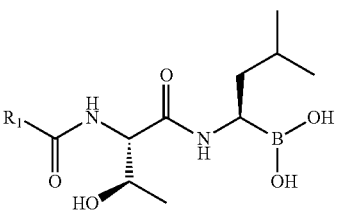

or a pharmaceutically acceptable salt or ester thereof.

Embodiment #4

The lyophilized cake of Embodiment 1 or the method of Embodiment 1A, wherein the drug is a compound of Formula I, Formula II, or a pharmaceutically acceptable ester thereof.

Embodiment #4A

The lyophilized cake of Embodiment 1 or the method of Embodiment 1A, wherein the drug is a compound of Formula I or a pharmaceutically acceptable ester thereof.

Embodiment #4B

The lyophilized cake of Embodiment 1 or the method of Embodiment 1A, wherein the drug is a compound of Formula II or a pharmaceutically acceptable ester thereof.

Embodiment #5

The lyophilized cake of Embodiment 1 or the method of Embodiment 1A, wherein the drug is a compound of Formula I or Formula II.

Embodiment #5A

The lyophilized cake of Embodiment 1 or the method of Embodiment 1A, wherein the drug is a compound of Formula I.

Embodiment #5B

The lyophilized cake of Embodiment 1 or the method of Embodiment 1A, wherein the drug is a compound of Formula II.

Embodiment #6

The lyophilized cake or method of any one of the preceding Embodiments, wherein $R_1$ is optionally substituted pyrazinyl, pyridyl, phenyl, thiazolyl, naphthyl, or quinolinyl.

Embodiment #7

The lyophilized cake or method of any one of the preceding Embodiments, wherein $R_1$ is substituted.

Embodiment #8

The lyophilized cake or method of any one of the preceding Embodiments, wherein $R_1$ is a 5-membered heteroaryl substituted with phenyl, a 6-membered heteroaryl substituted with phenyl, or phenyl substituted with phenyl.

Embodiment #9

The lyophilized cake of Embodiment 1 or the method of Embodiment 1A, wherein the drug is Compound 1

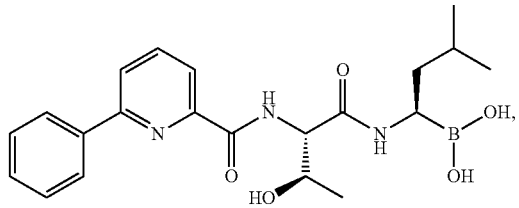

Compound 2

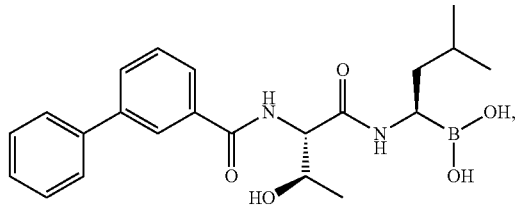

Compound 3

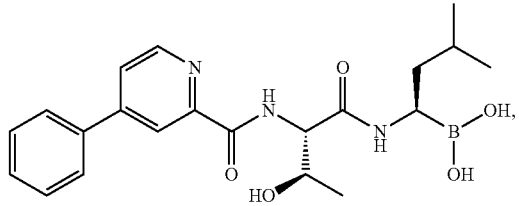

Compound 4

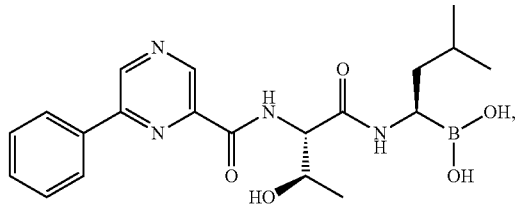

Compound 5

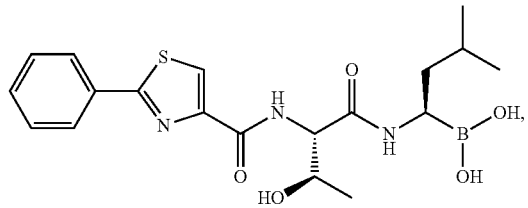

Compound 6

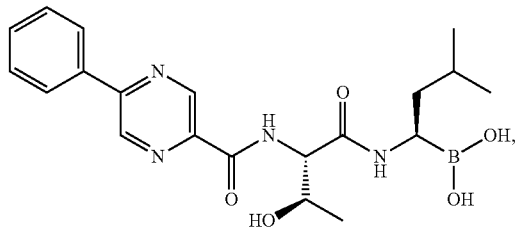

-continued

Compound 7

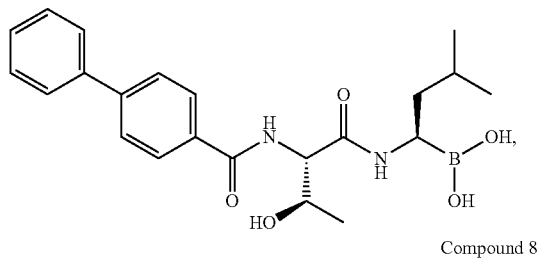

Compound 8

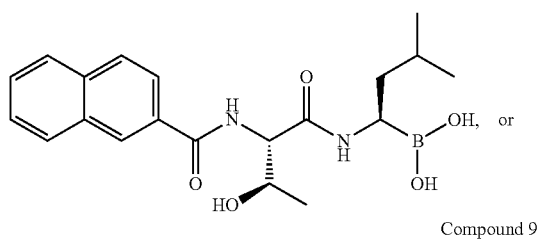

Compound 9

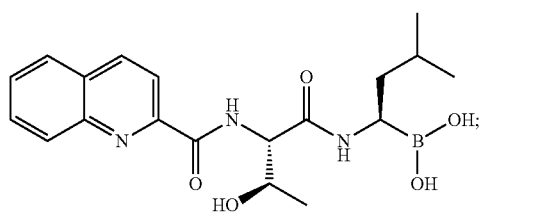

or a pharmaceutically acceptable salt or ester thereof.

Embodiment #9A

The lyophilized cake of Embodiment 1 or the method of Embodiment 1A, wherein the drug is Compound 1, Compound 2, Compound 3, Compound 4, Compound 5, Compound 6, Compound 7, Compound 8, Compound 9, or a pharmaceutically acceptable ester thereof.

Embodiment #9B

The lyophilized cake of Embodiment 1 or the method of Embodiment 1A, wherein the drug is Compound 1, Compound 2, Compound 3, Compound 4, Compound 5, Compound 6, Compound 7, Compound 8, or Compound 9.

Embodiment #10

The lyophilized cake of Embodiment 1 or the method of Embodiment 1A, wherein the drug is a compound of formula:

Compound 1

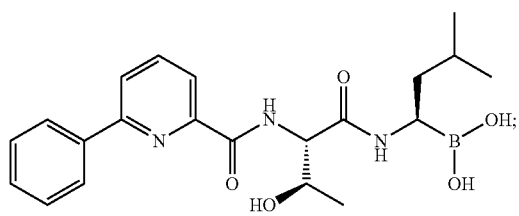

or a pharmaceutically acceptable salt or ester thereof.

Embodiment #10A

The lyophilized cake of Embodiment 1 or the method of Embodiment 1A, wherein the drug is Compound 1, Compound 10, Compound 11, Compound 12, Compound 13, Compound 14, Compound 15, or bortezomib.

Embodiment #10B

The lyophilized cake of Embodiment 1 or the method of Embodiment 1A, wherein the drug is Compound 1, Compound 10, Compound 11, Compound 13, or bortezomib.

Embodiment #10C

The lyophilized cake of Embodiment 1 or the method of Embodiment 1A, wherein the drug is Compound 1, Compound 10, Compound 13, or bortezomib.

Embodiment #10D

The lyophilized cake of Embodiment 1 or the method of Embodiment 1A, wherein the drug is Compound 1, Compound 10, or Compound 13.

Embodiment #10E

The lyophilized cake of Embodiment 1 or the method of Embodiment 1A, wherein the drug is Compound 1 or Compound 10.

Embodiment #10F

The lyophilized cake of Embodiment 1 or the method of Embodiment 1A, wherein the drug is Compound 10.

Embodiment #10G

The lyophilized cake of Embodiment 1 or the method of Embodiment 1A, wherein the drug is Compound 1 or bortezomib.

Embodiment #10H

The lyophilized cake of Embodiment 1 or the method of Embodiment 1A, wherein the drug is Compound 1.

Embodiment #10I

The lyophilized cake of Embodiment 1 or the method of Embodiment 1A, wherein the drug is bortezomib.

Embodiment #11

The lyophilized cake of Embodiment 1 or the method of Embodiment 1A, wherein the drug is a compound of Formula II or a pharmaceutically acceptable salt or ester thereof.

Embodiment #12

The lyophilized cake or method of any one of the preceding Embodiments, wherein the lyophilized cake comprises at least one bulking agent.

Embodiment #13

The lyophilized cake or method of Embodiment 12, wherein the lyophilized cake comprises up to about 99% w/w of the bulking agent.

Embodiment #14

The lyophilized cake or method of Embodiment 12, wherein the lyophilized cake comprises about 20% to about 90% w/w of the bulking agent.

Embodiment #15

The lyophilized cake or method of Embodiment 12, wherein the lyophilized cake comprises about 30% to about 60% w/w of the bulking agent.

Embodiment #16

The lyophilized cake or method of Embodiment 12, wherein the lyophilized cake comprises about 35% of the bulking agent.

Embodiment #17

The lyophilized cake or method of Embodiment 12, wherein the lyophilized cake comprises about 45% w/w of the bulking agent.

Embodiment #18

The lyophilized cake or method of any one of Embodiments 12-17, wherein the bulking agent is a monosaccharide, an oligosaccharide, a sugar alcohol, an amino acid, or a mixture thereof.

Embodiment #19

The lyophilized cake or method of Embodiment 18, wherein the bulking agent comprises sucrose, dextrose, maltose, a dextran, or a mixture thereof.

Embodiment #20

The lyophilized cake or method of Embodiment 18, wherein the bulking agent comprises mannitol.

Embodiment #20A

The lyophilized cake or method of any of the preceding Embodiments, wherein the lyophilized cake does not contain a surfactant.

Embodiment #21

The lyophilized cake or method of any of Embodiments 1-20, wherein the lyophilized cake comprises at least one surfactant.

Embodiment #22

The lyophilized cake or method of Embodiment 21, wherein the lyophilized cake comprises at least about 10% to about 40% w/w of the surfactant

Embodiment #23

The lyophilized cake or method of Embodiment 21, wherein the lyophilized cake comprises at least about 15% to about 30% w/w of the surfactant.

Embodiment #24

The lyophilized cake or method of Embodiment 21, wherein the lyophilized cake comprises at least about 15% to about 20% w/w of the surfactant.

Embodiment #25

The lyophilized cake or method of any one of Embodiments 21 to 24, wherein the surfactant is a polyoxyethylene stearate, polyoxyethylene castor oil derivatives, polyoxyethylene sorbitan fatty acid ester, sorbitan esters, polyethylene glycol ether, saturated polyglycolized glyceride, fatty acid ester of polyethylene glycol, hydroxylated lecithin, medium chain monoglyceride, medium chain fatty acid ester, polyethylene/propylene glycol copolymer, polyethylene glycol stearate, d-α-tocopheryl polyethylene glycol succinate, polyoxyl stearate, polyoxyl castor oil, saturated polyglycolized glyceride consisting of mono-, di-, or triglycerides; di-fatty acid esters of polyethylene glycol, hydroxylated lecithin; medium chain monoglyceride, medium chain monoglyceride and diglyceride; polyethylene/propylene glycol copolymer; block copolymer of ethylene oxide and propylene oxide, ethoxylated castor oil; ethoxylated hydroxystearic acid; or a mixture thereof.

Embodiment #26

The lyophilized cake or method of any one of Embodiments 21 to 24, wherein the surfactant is a polyoxypropylene polyoxyethylene block copolymer, a polysorbate, macrogol 15 hydroxy stearate, polyoxyl 35 castor oil, a polyoxyl castor oil, propylene glycol, or a mixture thereof.

Embodiment #27

The lyophilized cake or method of Embodiment 26, wherein the surfactant is a polysorbate.

Embodiment #28

The lyophilized cake or method of Embodiment 26, wherein the polysorbate is polysorbate 20.

Embodiment #29

The lyophilized cake or method of any of Embodiments 1-20 or 21-28, wherein the lyophilized cake comprises at least one bulking agent and at least one surfactant.

Embodiment #30

The lyophilized cake or method of any one of the preceding Embodiments, wherein the cyclodextrin is an α-cyclodextrin, a β-cyclodextrin, a γ-cyclodextrin, or a mixture thereof.

Embodiment #31

The lyophilized cake or method of any one of the preceding Embodiments, wherein the cyclodextrin is an alkylated cyclodextrin, a hydroxylalkylated cyclodextrin, a sulfoalkyl cyclodextrin, a saccharide-substituted cyclodextrin, or a mixture thereof.

Embodiment #32

The lyophilized cake or method of any one of the preceding Embodiments, wherein the cyclodextrin is methyl-β-cyclodextrin, dimethyl-β-cyclodextrin, trimethyl-β-cyclodextrin, 2-hydroxymethyl-β-cyclodextrin, hydroxyethyl-β-cyclodextrin, 2-hydroxypropyl-β-cyclodextrin, 3-hydroxypropyl-β-cyclodextrin, β-cyclodextrin sulfate, β-cyclodextrin sulfonate, β-cyclodextrin sulfobutyl ether, or a mixture thereof.

Embodiment #33

The lyophilized cake or method of any one of the preceding Embodiments, wherein the cyclodextrin is hydroxypropyl β cyclodextrin, hydroxypropyl γ cyclodextrin, sulfobutyl ether β cyclodextrin, or a mixture thereof.

Embodiment #34

The lyophilized cake or method of any one of the preceding Embodiments, wherein the cyclodextrin is hydroxypropyl β cyclodextrin, sulfobutyl ether β cyclodextrin, or a mixture thereof.

Embodiment #35

The lyophilized cake or method of any one of the preceding Embodiments, wherein the cyclodextrin is hydroxypropyl β cyclodextrin.

Embodiment #36

The lyophilized cake or method of any one of the preceding Embodiments, wherein the cyclodextrin is present in an amount up to about 99% w/w of the lyophilized cake.

Embodiment #37

The lyophilized cake or method of any one of the preceding Embodiments, wherein the cyclodextrin is present in an amount from about 20% to about 90% w/w of the lyophilized cake.

Embodiment #38

The lyophilized cake or method of any one of the preceding Embodiments, wherein the cyclodextrin is present in an amount from about 40% to about 70% w/w of the lyophilized cake.

Embodiment #39

The lyophilized cake or method of any one of the preceding Embodiments, wherein the cyclodextrin is present in an amount from about 45% to about 65% w/w of the lyophilized cake.

Embodiment #40

The lyophilized cake or method of any one of the preceding Embodiments, wherein the cyclodextrin is present in an amount of about 40% w/w of the lyophilized cake.

Embodiment #41

The lyophilized cake or method of any one of the preceding Embodiments, wherein the cyclodextrin is present in an amount of about 45% w/w of the lyophilized cake

Embodiment #42

The lyophilized cake or method of any one of the preceding Embodiments, wherein the cyclodextrin is present in an amount of about 55% w/w of the lyophilized cake.

Embodiment #43

The lyophilized cake or method of any one of the preceding Embodiments, wherein the lyophilized cake further comprises a pharmaceutically acceptable organic solvent.

Embodiment #44

The lyophilized cake or method of Embodiment 43, wherein the organic solvent is dimethylsulfoxide, ethanol, propanol, tert-butanol, or a mixture thereof.

Embodiment #45

The lyophilized cake or method of Embodiment 43, wherein the organic solvent is tert-butanol.

Embodiment #46

The lyophilized cake or method of Embodiment 45, wherein the tert-butanol is present in an amount of about 3% w/w, or less.

Embodiment #47

The lyophilized cake or method of Embodiment 45, wherein the tert-butanol is present in an amount of about 1% w/w, or less.

Embodiment #48

The lyophilized cake or method of any one of the preceding Embodiments, wherein the lyophilized cake further comprises a pH modifier.

Embodiment #48A

The lyophilized cake or method of Embodiment 48, wherein the pH modifier comprises an acid.

Embodiment #48B

The lyophilized cake or method of Embodiment 48, wherein the pH modifier comprises a mineral acid or an organic acid.

Embodiment #48C

The lyophilized cake or method of Embodiment 48, wherein the pH modifier comprises a mineral acid.

Embodiment #48D

The lyophilized cake or method of Embodiment 48, wherein the pH modifier comprises an organic acid.

Embodiment #48E

The lyophilized cake or method of Embodiment 48, wherein the pH modifier comprises at least acid chosen from hydrochloric acid, phosphoric acid, acetic acid, sulfuric acid, ascorbic acid, citric acid, lactic acid, tartaric acid, succinic acid, and maleic acid.

Embodiment #48F

The lyophilized cake or method of Embodiment 48, wherein the pH modifier comprises phosphoric acid.

Embodiment #48G

The lyophilized cake or method of any of Embodiments 48A-48F, wherein the pH of the lyophilized cake is adjusted to a pH of about 7 or lower.

Embodiment #48H

The lyophilized cake or method of any of Embodiments 48A-48F, wherein the pH of the lyophilized cake is adjusted to a pH of about 6 or lower.

Embodiment #48I

The lyophilized cake or method of any of Embodiments 48A-48F, wherein the pH of the lyophilized cake is adjusted to a pH of about 5 or lower.

Embodiment #48J

The lyophilized cake or method of any of Embodiments 48A-48F, wherein the pH of the lyophilized cake is adjusted to a pH of about 4 or lower.

Embodiment #48K

The lyophilized cake or method of any of Embodiments 48A-48F, wherein the pH of the lyophilized cake is adjusted to a pH of about 3-5.

Embodiment #48L

The lyophilized cake or method of any of Embodiments 48A-48F, wherein the pH of the lyophilized cake is adjusted to a pH of about 4.

Embodiment #49

The lyophilized cake or method of any one of the preceding Embodiments wherein the lyophilized cake reconstitutes in about 180 seconds or less to provide a clear solution free of particulate matter.

Embodiment #49A

The lyophilized cake or method of any one of the preceding Embodiments wherein the lyophilized cake reconstitutes in about 90 seconds or less to provide a clear solution free of particulate matter.

Embodiment #49B

The lyophilized cake or method of any one of the preceding Embodiments wherein the lyophilized cake reconstitutes in about 30 seconds or less to provide a clear solution free of particulate matter.

Embodiment #50

The lyophilized cake or method of any one of Embodiments 49-49B wherein the reconstituted solution is colorless.

Embodiment #51

The lyophilized cake or method of any one of the preceding Embodiments wherein the lyophilized cake is stable for at least 6 months during storage under refrigerated conditions.

Embodiment #52

The lyophilized cake or method of any one of the preceding Embodiments wherein the lyophilized cake is stable for at least 6 months during storage under room temperature conditions.

Embodiment #53

The lyophilized cake or method of any one of the preceding Embodiments wherein the lyophilized cake is stable for at least 6 months during storage under accelerated conditions.

Embodiment #54

The lyophilized cake or method of any one of the preceding Embodiments, wherein the lyophilized cake exhibits a decrease in drug purity of no more than about 1% after storage for 6 months under refrigerated conditions.

Embodiment #55

The lyophilized cake or method of any one of the preceding Embodiments, wherein the lyophilized cake exhibits a decrease in drug purity of no more than about 1% after storage for 6 months under room temperature conditions.

Embodiment #56

The lyophilized cake or method of any one of the preceding Embodiments, wherein the lyophilized cake exhibits a decrease in drug purity of no more than about 1% after storage for 6 months under accelerated conditions.

Embodiment #57

The lyophilized cake or method of any one of the preceding Embodiments, wherein the lyophilized cake exhibits a decrease in drug purity of no more than about 0.5% after storage for 6 months under refrigerated conditions.

Embodiment #58

The lyophilized cake or method of any one of the preceding Embodiments, wherein the lyophilized cake exhibits a decrease in drug purity of no more than about 0.5% after storage for 6 months under room temperature conditions.

Embodiment #59

The lyophilized cake or method of any one of the preceding Embodiments, wherein the lyophilized cake exhibits a decrease in drug purity of no more than about 0.5% after storage for 6 months under accelerated conditions.

Embodiment #60

The lyophilized cake or method of any one of the preceding Embodiments, wherein the lyophilized cake contains no more than about 0.5% w/w of degradation impurities after storage of the cake for six months under refrigerated conditions.

Embodiment #60A

The lyophilized cake or method of any one of the preceding Embodiments, wherein the lyophilized cake contains no more than about 0.2% w/w of degradation impurities after storage of the cake for six months under refrigerated conditions.

Embodiment #60B

The lyophilized cake or method of any one of the preceding Embodiments, wherein the lyophilized cake contains no more than about 0.1% w/w of degradation impurities after storage of the cake for six months under refrigerated conditions.

Embodiment #60C

The lyophilized cake or method of any one of the preceding Embodiments, wherein the lyophilized cake contains no more than about 0.5% w/w of degradation impurities after storage of the cake for twelve months under refrigerated conditions.

Embodiment #60D

The lyophilized cake or method of any one of the preceding Embodiments, wherein the lyophilized cake contains no more than about 0.2% w/w of degradation impurities after storage of the cake for twelve months under refrigerated conditions.

Embodiment #60E

The lyophilized cake or method of any one of the preceding Embodiments, wherein the lyophilized cake contains no more than about 0.1% w/w of degradation impurities after storage of the cake for twelve months under refrigerated conditions.

Embodiment #60F

The lyophilized cake or method of any one of the preceding Embodiments, wherein the lyophilized cake contains no more than about 0.5% w/w of degradation impurities after storage of the cake for six months under room temperature conditions.

Embodiment #60G

The lyophilized cake or method of any one of the preceding Embodiments, wherein the lyophilized cake contains no more than about 0.2% w/w of degradation impurities after storage of the cake for six months under room temperature conditions.

Embodiment #60H

The lyophilized cake or method of any one of the preceding Embodiments, wherein the lyophilized cake contains no more than about 0.1% w/w of degradation impurities after storage of the cake for six months under room temperature conditions.

Embodiment #60I

The lyophilized cake or method of any one of the preceding Embodiments, wherein the lyophilized cake contains no more than about 0.5% w/w of degradation impurities after storage of the cake for twelve months under room temperature conditions.

Embodiment #60J

The lyophilized cake or method of any one of the preceding Embodiments, wherein the lyophilized cake contains no more than about 0.2% w/w of degradation impurities after storage of the cake for twelve months under room temperature conditions.

Embodiment #60K

The lyophilized cake or method of any one of the preceding Embodiments, wherein the lyophilized cake contains no more than about 0.1% w/w of degradation impurities after storage of the cake for twelve months under room temperature conditions.

Embodiment #60L

The lyophilized cake or method of any one of the preceding Embodiments, wherein the lyophilized cake contains no more than about 0.5% w/w of degradation impurities after storage of the cake for six months under enhanced room temperature conditions.

Embodiment #60M

The lyophilized cake or method of any one of the preceding Embodiments, wherein the lyophilized cake contains no more than about 0.2% w/w of degradation impurities after storage of the cake for six months under enhanced room temperature conditions.

Embodiment #60N

The lyophilized cake or method of any one of the preceding Embodiments, wherein the lyophilized cake contains no more than about 0.1% w/w of degradation impurities after storage of the cake for six months under enhanced room temperature conditions.

Embodiment #60O

The lyophilized cake or method of any one of the preceding Embodiments, wherein the lyophilized cake contains no more than about 0.5% w/w of degradation impurities after storage of the cake for twelve months under enhanced room temperature conditions.

Embodiment #60P

The lyophilized cake or method of any one of the preceding Embodiments, wherein the lyophilized cake contains no more than about 0.2% w/w of degradation impurities after storage of the cake for twelve months under enhanced room temperature conditions.

Embodiment #60Q

The lyophilized cake or method of any one of the preceding Embodiments, wherein the lyophilized cake contains no more than about 0.1% w/w of degradation impurities after storage of the cake for twelve months under enhanced room temperature conditions.

Embodiment #60R

The lyophilized cake or method of any one of the preceding Embodiments, wherein the lyophilized cake contains no more than about 0.5% w/w of degradation impurities after storage of the cake for six months under accelerated conditions.

Embodiment #60S

The lyophilized cake or method of any one of the preceding Embodiments, wherein the lyophilized cake contains no more than about 0.2% w/w of degradation impurities after storage of the cake for six months under accelerated conditions.

Embodiment #60T

The lyophilized cake or method of any one of the preceding Embodiments, wherein the lyophilized cake contains no more than about 0.1% w/w of degradation impurities after storage of the cake for six months under accelerated conditions.

Embodiment #60U

The lyophilized cake or method of any one of the preceding Embodiments, wherein the lyophilized cake contains no more than about 0.5% w/w of degradation impurities after storage of the cake for twelve months under accelerated conditions.

Embodiment #60V

The lyophilized cake or method of any one of the preceding Embodiments, wherein the lyophilized cake contains no more than about 0.2% w/w of degradation impurities after storage of the cake for twelve months under accelerated conditions.

Embodiment #60W

The lyophilized cake or method of any one of the preceding Embodiments, wherein the lyophilized cake contains no more than about 0.1% w/w of degradation impurities after storage of the cake for twelve months under accelerated conditions.

Embodiment #61

The lyophilized cake or method of any one of the preceding Embodiments, further comprising at least one additional antineoplastic agent.

Embodiment #62

A method for manufacturing a lyophilized cake comprising (a) providing a first mixture comprising a cyclodextrin, a bulking agent, and water;
(b) mixing a surfactant and a portion of the first mixture to form a second mixture;
(c) combining a compound of Formula I or Formula II, or a salt or ester thereof, and the second mixture to form a drug mixture;
(d) mixing the remainder of the first mixture with the drug mixture to form a pre-lyophilization solution; and
(e) lyophilizing the pre-lyophilization solution.

Embodiment #63

The method of Embodiment 62, wherein the cyclodextrin comprises hydroxypropyl β cyclodextrin and the bulking agent comprises mannitol.

Embodiment #64

The method of Embodiment 62, wherein the surfactant is a polysorbate.

Embodiment #65

The method of any one of Embodiments 62 to 64 further comprising sterilizing the pre-lyophilization solution.

Embodiment #66

The method of Embodiment 65, wherein the sterilizing step comprises filtration.

Embodiment #67

A method for manufacturing a lyophilized cake comprising:
(a) providing a first mixture containing a cyclodextrin, a bulking agent, and water;
(b) providing a drug mixture containing a compound of Formula I or Formula II, or a salt or ester thereof, and tert-butanol;
(c) combining the first mixture and the drug mixture to provide a pre-lyophilization solution; and
(d) lyophilizing the pre-lyophilization solution.

Embodiment #68

The method of Embodiment 67, wherein the cyclodextrin is hydroxypropyl β cyclodextrin and the bulking agent comprises mannitol.

Embodiment #69

The method of Embodiment 67 or 68 further comprising the step of sterilizing the pre-lyophilization solution.

Embodiment #70

The method of Embodiment 69, wherein the sterilizing step comprises filtration.

Embodiment #71

The method of any of Embodiments 62-70, wherein the drug mixture contains a compound of Formula I, Formula II, or a pharmaceutically acceptable ester thereof.

Embodiment #72

The method of any of Embodiments 62-70, wherein the drug mixture contains a compound of Formula I or a pharmaceutically acceptable ester thereof.

Embodiment #73

The method of any of Embodiments 62-70, wherein the drug mixture contains a compound of Formula II or a pharmaceutically acceptable ester thereof.

Embodiment #74

The method of any of Embodiments 62-70, wherein the drug mixture contains a compound of Formula I or Formula II.

Embodiment #75

The method of any of Embodiments 62-70, wherein the drug mixture contains a compound of Formula I.

Embodiment #76

The method of any of Embodiments 62-70, wherein the drug mixture contains a compound of Formula II.

Embodiment #77

The method of any of Embodiments 62-76, wherein $R_1$ is optionally substituted pyrazinyl, pyridyl, phenyl, thiazolyl, naphthyl, or quinolinyl.

Embodiment #78

The method of any of Embodiments 62-77, wherein $R_1$ is substituted.

Embodiment #79

The method of any of Embodiments 62-76, wherein $R_1$ is a 5-membered heteroaryl substituted with phenyl, a 6-membered heteroaryl substituted with phenyl, or phenyl substituted with phenyl.

Embodiment #80

The method of any of Embodiments 62-70, wherein the drug mixture contains

Compound 1

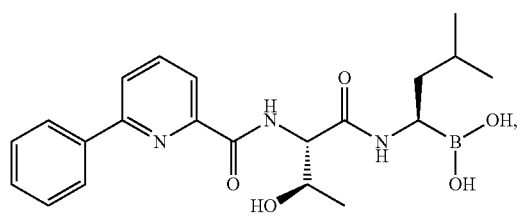

Compound 2

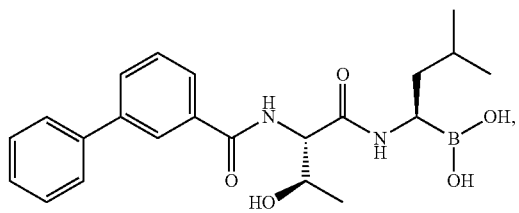

Compound 3

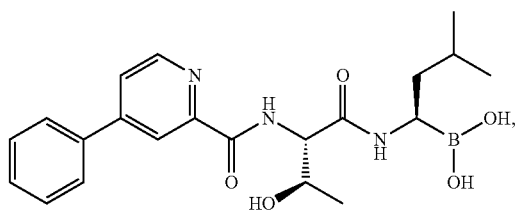

Compound 4

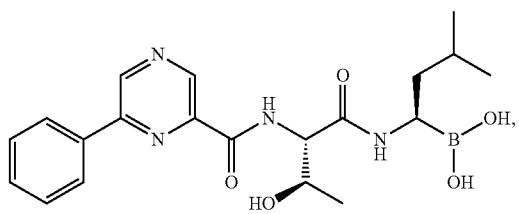

Compound 5

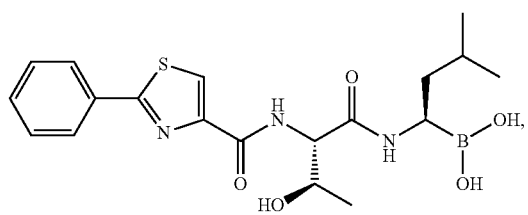

Compound 6

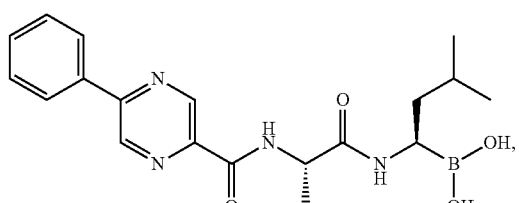

Compound 7

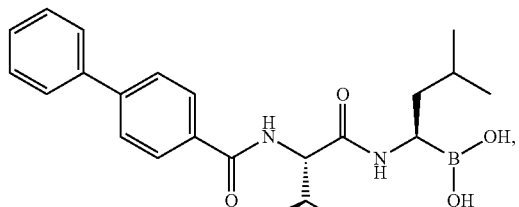

-continued

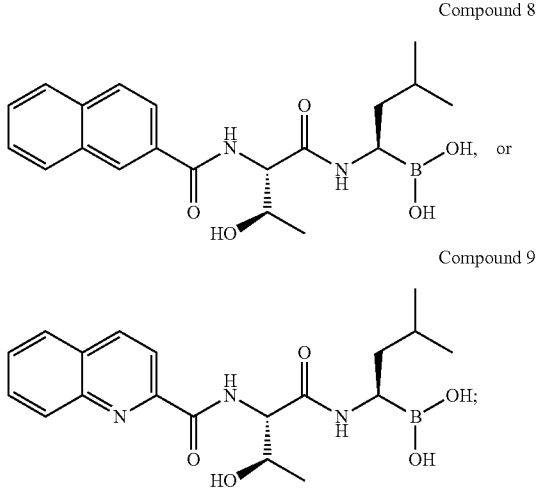

Compound 8

Compound 9 or a pharmaceutically acceptable salt or ester thereof.

Embodiment #81

The method of any of Embodiments 62-70, wherein the drug mixture contains Compound 1, Compound 2, Compound 3, Compound 4, Compound 5, Compound 6, Compound 7, Compound 8, Compound 9, or a pharmaceutically acceptable ester thereof.

Embodiment #82

The method of any of Embodiments 62-70, wherein the drug mixture contains Compound 1, Compound 2, Compound 3, Compound 4, Compound 5, Compound 6, Compound 7, Compound 8, or Compound 9.

Embodiment #83

The method of any of Embodiments 62-70, wherein the drug mixture contains a compound of formula:

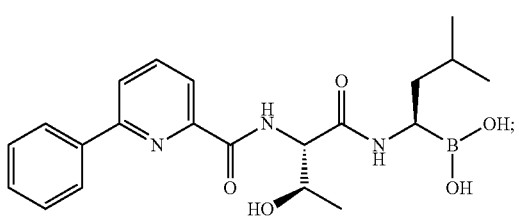

Compound 1 or a pharmaceutically acceptable salt or ester thereof.

Embodiment #84

The method of any of Embodiments 62-70, wherein the drug mixture contains Compound 1, Compound 10, Compound 11, Compound 12, Compound 13, Compound 14, Compound 15, or bortezomib.

Embodiment #85

The method of any of Embodiments 62-70, wherein the drug mixture contains Compound 1, Compound 10, Compound 11, Compound 13, or bortezomib.

Embodiment #86

The method of any of Embodiments 62-70, wherein the drug mixture contains Compound 1, Compound 10, Compound 13, or bortezomib.

Embodiment #87

The method of any of Embodiments 62-70, wherein the drug mixture contains Compound 1, Compound 10, or Compound 13.

Embodiment #88

The method of any of Embodiments 62-70, wherein the drug mixture contains Compound 1 or Compound 10.

Embodiment #89

The method of any of Embodiments 62-70, wherein the drug mixture contains Compound 10.

Embodiment #90

The method of any of Embodiments 62-70, wherein the drug mixture contains Compound 1 or bortezomib.

Embodiment #91

The method of any of Embodiments 62-70, wherein the drug mixture contains Compound 1.

Embodiment #92

The method of any of Embodiments 62-70, wherein the drug mixture contains bortezomib.

Embodiment #93

The method of any of Embodiments 62-70, wherein the drug mixture contains a compound of Formula II or a pharmaceutically acceptable salt or ester thereof.

Embodiment #94

The method of any of Embodiments 62-93, further comprising the step of adjusting the pH of the pre-lyophilization solution with a pH modifier.

Embodiment #95

The method of Embodiment 94, wherein the pH modifier comprises an acid.

Embodiment #96

The method of Embodiment 94, wherein the pH modifier comprises a mineral acid or an organic acid.

Embodiment #97

The method of Embodiment 94, wherein the pH modifier comprises a mineral acid.

Embodiment #98

The method of Embodiment 94, wherein the pH modifier comprises an organic acid.

Embodiment #99

The method of Embodiment 94, wherein the pH modifier comprises at least acid chosen from hydrochloric acid, phosphoric acid, acetic acid, sulfuric acid, ascorbic acid, citric acid, lactic acid, tartaric acid, succinic acid, and maleic acid.

Embodiment #100

The method of Embodiment 94, wherein the pH modifier comprises phosphoric acid.

Embodiment #101

The method of any of Embodiments 95-100, wherein the pH of the pre-lyophilization solution is adjusted to a pH of about 7 or lower.

Embodiment #102

The method of any of Embodiments 95-100, wherein the pH of the pre-lyophilization solution is adjusted to a pH of about 6 or lower.

Embodiment #103

The method of any of Embodiments 95-100, wherein the pH of the pre-lyophilization solution is adjusted to a pH of about 5 or lower.

Embodiment #104

The method of any of Embodiments 95-100, wherein the pH of the pre-lyophilization solution is adjusted to a pH of about 4 or lower.

Embodiment #105

The method of any of Embodiments 95-100, wherein the pH of the pre-lyophilization solution is adjusted to a pH of about 3-5.

Embodiment #106

The method of any of Embodiments 95-100, wherein the pH of the pre-lyophilization solution is adjusted to a pH of about 4.

Embodiment #107

Use of the lyophilized cake of any of Embodiments 1 to 61 in the manufacture of a medicament for treating cancer.

Embodiment #108

Use of the lyophilized cake of any of Embodiments 1 to 61 in the manufacture of a medicament for treating chronic lymphocytic leukemia, Hodgkin's disease, non-Hodgkin's lymphoma, multiple myeloma or breast cancer.

Embodiment #109

Use of the lyophilized cake of any of Embodiments 1 to 61 in the manufacture of a medicament for treating multiple myeloma.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

All publications referenced herein are incorporated by reference in their entireties for all purposes.

What is claimed:

1. A lyophilized cake comprising:
   (a) a compound of Formula I or a pharmaceutically acceptable salt or ester thereof:

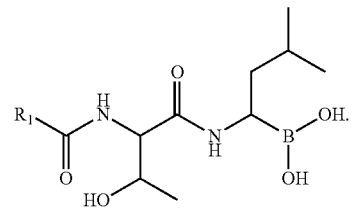

I wherein $R_1$ is an optionally substituted 5-, 6-, or 10-membered heteroaryl having at least one N or $R_1$ is an optionally substituted 6- or 10-membered aryl;
   (b) a cyclodextrin; and
   (c) a bulking agent comprising a monosaccharide.

2. The lyophilized cake of claim 1, wherein the compound of Formula I is

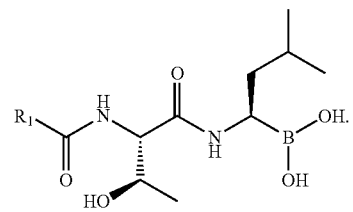

3. The lyophilized cake of claim 1, wherein the compound of Formula I is Compound 1

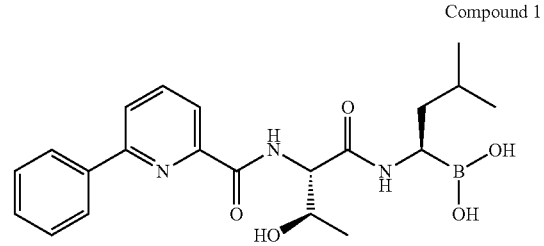 [SMILES: CC(C)C[C@H](NC(=O)[C@@H](NC(=O)c1cccc(-c2ccccc2)n1)[C@@H](C)O)B(O)O]

Compound 1 or a pharmaceutically acceptable salt or ester thereof.

4. The lyophilized cake of claim 3, wherein the drug is Compound 1.

5. The lyophilized cake of claim 3, further comprising a surfactant.

6. The lyophilized cake of claim 3, wherein the cyclodextrin is methyl-β-cyclodextrin, dimethyl-β-cyclodextrin, trimethyl-β-cyclodextrin, 2-hydroxymethyl-β-cyclodextrin, hydroxyethyl-β-cyclodextrin, 2-hydroxypropyl-β-cyclodextrin, 3-hydroxypropyl-β-cyclodextrin, β-cyclodextrin sulfate, β-cyclodextrin sulfonate, β-cyclodextrin sulfobutyl ether, or a mixture thereof.

7. The lyophilized cake of claim 3, wherein the lyophilized cake reconstitutes in about 90 seconds or less to provide a clear solution free of particulate matter.

8. The lyophilized cake of claim 3, further comprising a pH modifier.

9. The lyophilized cake of claim 8, wherein the pH modifier comprises an acid.

10. The lyophilized cake of claim 9, wherein the pH of the lyophilized cake is adjusted to a pH of about 4 or lower.

11. The lyophilized cake of claim 3, wherein the lyophilized cake exhibits a decrease in drug purity of no more than about 1% after storage for 6 months under accelerated conditions.

12. The lyophilized cake of claim 7, wherein the lyophilized cake exhibits a decrease in drug purity of no more than about 1% after storage for 6 months under accelerated conditions.

13. The lyophilized cake of claim 7, wherein the lyophilized cake exhibits a decrease in drug purity of no more than about 0.5% after storage for 6 month under accelerated conditions.

14. A method for manufacturing a lyophilized cake comprising the steps of:
   (a) providing a first mixture comprising a cyclodextrin, a bulking agent comprising a monosaccharide, and water;
   (b) mixing a surfactant and a portion of the first mixture to form a second mixture;
   (c) combining a compound of Formula I, or a salt or ester thereof, and the second mixture to form a drug mixture;

I

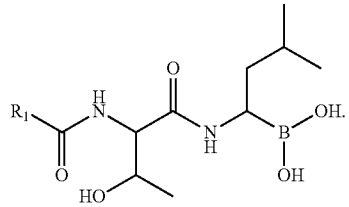

wherein $R_1$ is an optionally substituted 5-, 6-, or 10-membered heteroaryl having at least one N or $R_1$ is an optionally substituted 6- or 10-membered aryl;

(d) mixing the remainder of the first mixture with the drug mixture to form a pre-lyophilization solution; and
(e) lyophilizing the pre-lyophilization solution.

15. A method for manufacturing a lyophilized cake comprising:
   (a) providing a first mixture containing a cyclodextrin, a bulking agent comprising a monosaccharide, and water;
   (b) providing a drug mixture containing a compound of Formula I, or a salt or ester thereof, and tert-butanol;

I

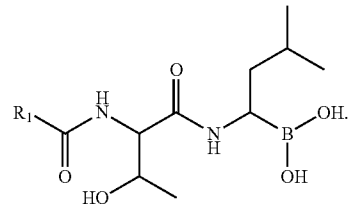

wherein $R_1$ is an optionally substituted 5-, 6-, or 10-membered heteroaryl having at least one N or $R_1$ is an optionally substituted 6- or 10-membered aryl;
   (c) combining the first mixture and the drug mixture to provide a pre-lyophilization solution; and
   (d) lyophilizing the pre-lyophilization solution.

16. The method of claim 14, wherein the drug mixture contains Compound 10

Compound 10

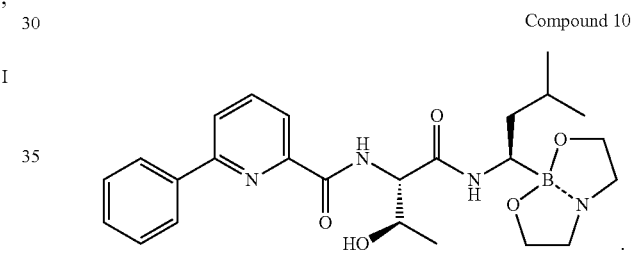

17. The method of claim 15, further comprising the step of adjusting the pH of the pre-lyophilization solution to a pH of about 4 or lower.

* * * * *

UNITED STATES PATENT AND TRADEMARK OFFICE
CERTIFICATE OF CORRECTION

PATENT NO. : 8,785,418 B2  Page 1 of 1
APPLICATION NO. : 13/248398
DATED : July 22, 2014
INVENTOR(S) : Denis Bricout et al.

It is certified that error appears in the above-identified patent and that said Letters Patent is hereby corrected as shown below:

In the Claims

Column 64,
Claim 1, line 27, delete "monosaccharide." and insert -- sugar alcohol. --.

Column 65,
Claim 14, line 25, delete "monosaccharide," and insert -- sugar alcohol, --.

Column 66,
Claim 15, line 7, delete "monosaccharide," and insert -- sugar alcohol, --.

Signed and Sealed this
Tenth Day of February, 2015

Michelle K. Lee
*Deputy Director of the United States Patent and Trademark Office*

UNITED STATES PATENT AND TRADEMARK OFFICE
CERTIFICATE OF CORRECTION

PATENT NO.       : 8,785,418 B2                                Page 1 of 1
APPLICATION NO.  : 13/248398
DATED            : July 22, 2014
INVENTOR(S)      : Denis Bricout et al.

It is certified that error appears in the above-identified patent and that said Letters Patent is hereby corrected as shown below:

In the Claims

<u>Column 64,</u>
Claim 4, line 57, delete "drug" and insert -- compound of Formula I --.

Signed and Sealed this
Twenty-sixth Day of May, 2015

Michelle K. Lee
*Director of the United States Patent and Trademark Office*